US012723068B2

(12) United States Patent
Schneeweiss

(10) Patent No.: US 12,723,068 B2
(45) Date of Patent: Sep. 1, 2026

(54) STABILIZED MHC I

(71) Applicant: IMUSYN GMBH & CO. KG, Hannover (DE)

(72) Inventor: Clemens Schneeweiss, Hannover (DE)

(73) Assignee: Imusyn GmbH & Co. KG, Hannover (DE)

( * ) Notice: Subject to any disclaimer, the term of this patent is extended or adjusted under 35 U.S.C. 154(b) by 1273 days.

(21) Appl. No.: 17/439,485

(22) PCT Filed: Apr. 2, 2020

(86) PCT No.: PCT/EP2020/059472

§ 371 (c)(1),
(2) Date: Sep. 15, 2021

(87) PCT Pub. No.: WO2020/201467

PCT Pub. Date: Oct. 8, 2020

(65) Prior Publication Data

US 2022/0153808 A1 May 19, 2022

(30) Foreign Application Priority Data

Apr. 2, 2019 (EP) .................................... 19166923

(51) Int. Cl.
*C07K 14/705* (2006.01)

(52) U.S. Cl.
CPC .............................. *C07K 14/70539* (2013.01)

(58) Field of Classification Search
None
See application file for complete search history.

(56) References Cited

U.S. PATENT DOCUMENTS 6,248,564 B1 6/2001 Walter et al.
6,682,741 B1 1/2004 Ribaudo et al.
2013/0171668 A1 7/2013 LØset
2019/0153065 A1 5/2019 Garrett-Thomson et al.
2020/0148744 A1 5/2020 Seidel, III et al.

OTHER PUBLICATIONS

Shields et al., "The Effect of Human ß2-Microglobulin on Major Histocompatibility Complex I Peptide Loading and the Engineering of a High Affinity Variant", The Journal of Biological Chemistry, 1998, pp. 28010-28018, vol. 273, No. 43, Elsevier Inc.
Hein et al., "Peptide-independent stabilization of MHC class I molecules breaches cellular quality control", Journal of Cell Science, 2014, pp. 2885-2897, vol. 127, The Company of Biologists Ltd.
IPD-IMGT/HLA Database Release 3.45.1, Jul. 12, 2021 available online at https://www.ebi.ac.uk/ipd/imgt/hla/.
International Search Report and Written Opinion from the corresponding International Patent Application No. PCT/EP2020/059472, dated Jun. 30, 2020.
Shields, M.J., "Mapping of the monoclonal antibody W6/32: sensitivity to the amino terminus of beta2-microglobulin" Tissue Antigens , Feb. 26, 1998, pp. 567-570, vol. 51, No. 5.
Chandran, A., et al., "A Simple and Rapid Method for Quality Control of Major Histocompatibility Complex—Peptide Monomers by Flow" CytometryFrontiers in Immunology, Feb. 8, 2017, pp. 1-8, vol. 8, No. 96.
Shields, M., et al., "The Effect of Human b2-Microglobulin on Major Histocompatibility Complex I Peptide Loading and the Engineering of a High Affinity Variant", The Journal of Biological Chemistry, Oct. 23, 1998, pp. 28010-28018m vol. 273, No. 43.
Jackson et al., "Thromboinflammation: challenges of therapeutically targeting coagulation and other host defense mechanisms", Blood, Feb. 28, 2019, pp. vol. 906-918, vol. 133, No. 9.

*Primary Examiner* — Ruixiang Li
(74) *Attorney, Agent, or Firm* — Greer, Burns & Crain, Ltd.; Steven P. Fallon; E. Kate Berezutskaya

(57) ABSTRACT

Modified MHC I molecules that can be expressed in cell culture and can be more stable than natural MHC I molecules. An analytical process uses the modified MHC I molecules, e.g. for determination of antibodies in a serum sample directed against these MHC I molecules. MHC I is provided which has at least one covalent bond formed between a Cystein in the alpha chain and a Cystein in the β2-microglobulin.

13 Claims, 5 Drawing Sheets

Figure 4:
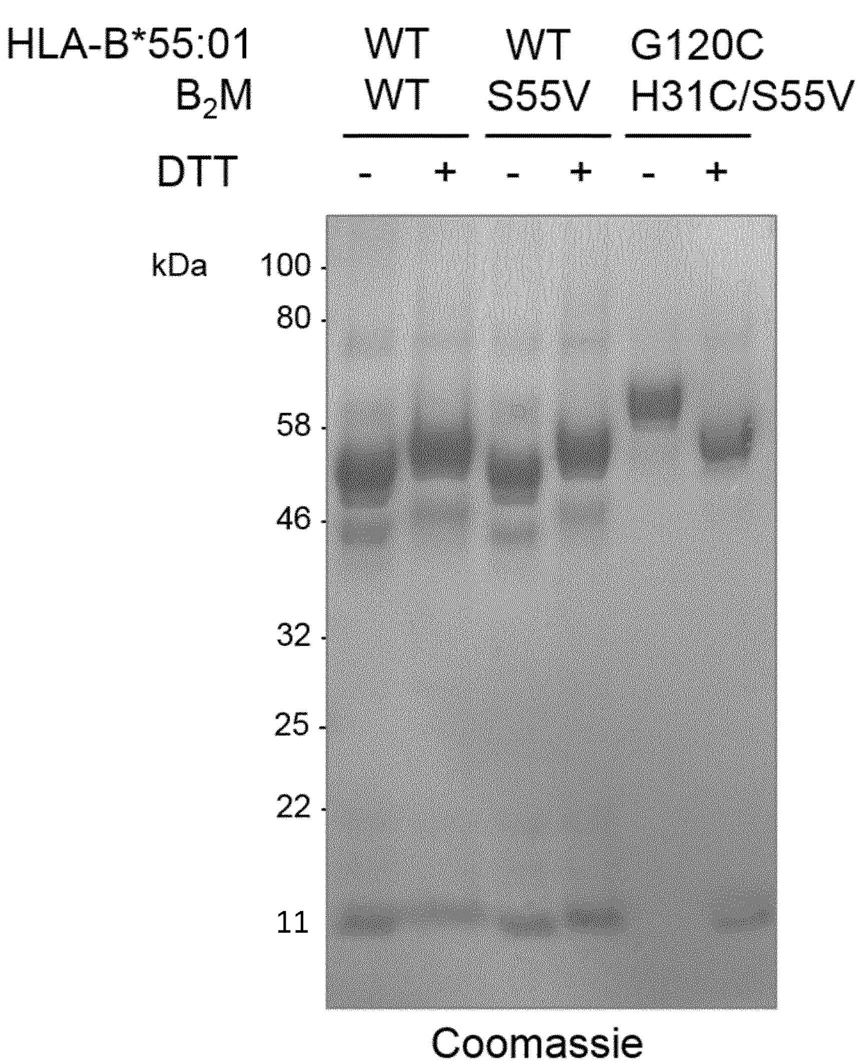

Specification includes a Sequence Listing.

Fig. 1
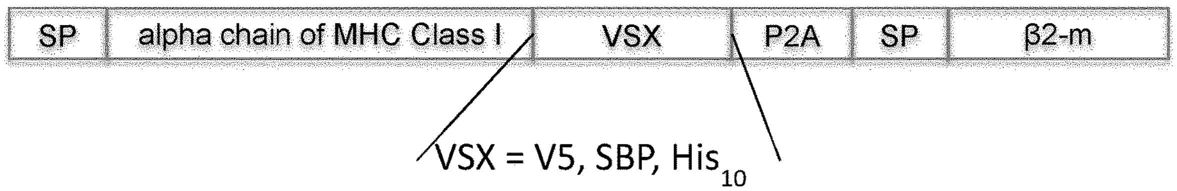
Fig. 2
Normalised
ng/ml
0,2
0,18
0,16
0,14
0,12
0,1
0,08
0,06
0,04
0,02
0
A236C/N24C_S55V G120C/H31C_S55V WT/WT WT/S55V
c_norm W6/32 (ng/ml) Wdh.
Fig. 3
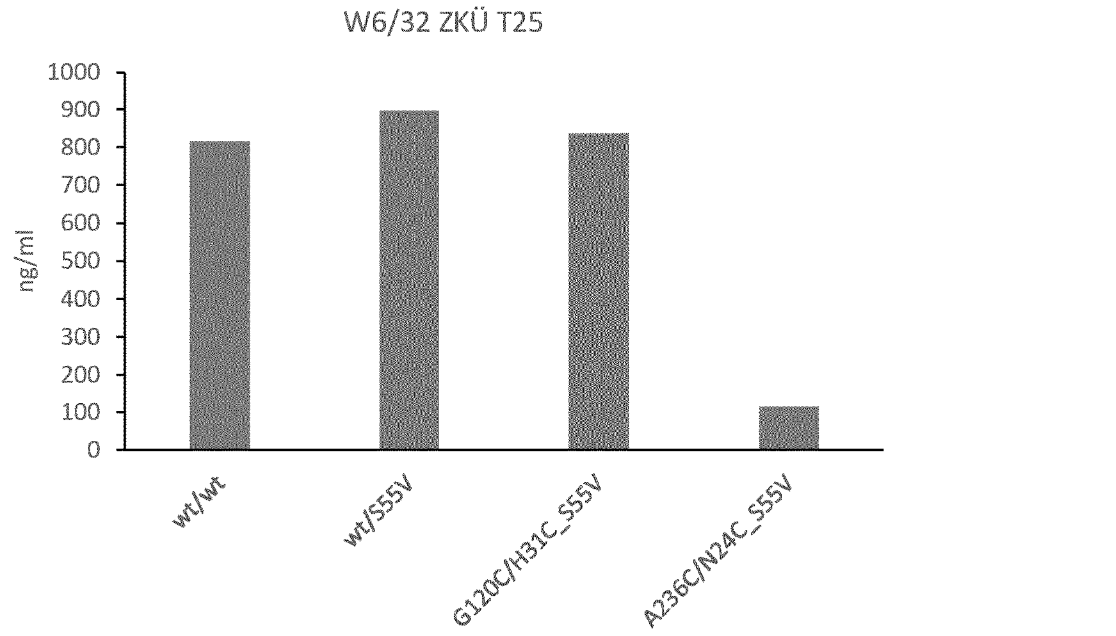

Fig. 6

```
As-Position      1       |           |          36
A*01:01:01:01    GSHSMRYFFTSVSRPGRGEPRFIAVGYVDDTQFVRF
B*07:02:01:01    GSHSMRYFYTSVSRPGRGEPRFISVGYVDDTQFVRF
C*01:02:01:01    CSHSMKYFFTSVSRPGRGEPRFISVGYVDDTQFVRF
                  ****.**:*************:************

As-Position      37                                                          96
A*01:01:01:01    DSDAASQKMEPRAPWIEQEGPEYWDQETRNMKAHSQTDRANLGTLRGYYNQSEDGSHTIQ
B*07:02:01:01    DSDAASPREEPRAPWIEQEGPEYWDRNTQIYKAQAQTDRESLRNLRGYYNQSEAGSHTLQ
C*01:02:01:01    DSDAASPRGEPRAPWVEQEGPEYWDRETQKYKRQAQTDRVSLRNLRGYYNQSEAGSHTLQ
                 ****** . ******:*********.:*.  * ::**** .* .********* ****:*

As-Position      97                       ||                                 156
A*01:01:01:01    IMYGCDVGPDGRFLRGYRQDAYDGKDYIALNEDLRSWTAADMAAQITKRKWEAVHAAEQR
B*07:02:01:01    SMYGCDVGPDGRLLRGHDQYAYDGKDYIALNEDLRSWTAADTAAQITQRKWEAAREAEQR
C*01:02:01:01    WMCGCDLGPDGRLLRGYDQYAYDGKDYIALNEDLRSWTAADTAAQITQRKWEAAREAEQR
                  * ***:*****:***: * ******************** *****:*****.. ****

As-Position      157                                                         216
A*01:01:01:01    RVYLEGRCVDGLRRYLENGKETLQRTDPPKTHMTHHPISDHEATLRCWALGFYPAEITLT
B*07:02:01:01    RAYLEGECVEWLRRYLENGKDKLERADPPKTHVTHHPISDHEATLRCWALGFYPAEITLT
C*01:02:01:01    RAYLEGTCVEWLRRYLENGKETLQRAEHPKTHVTHHPVSDHEATLRCWALGFYPAEITLT
                 *.**** **: *********:.*:*:: ****:****:**********************

As-Position      217                    ||                                   276
A*01:01:01:01    WQRDGEDQTQDTELVETRPAGDGTFQKWAAVVVPSGEEQRYTCHVQHEGLPKPLTLRWEL
B*07:02:01:01    WQRDGEDQTQDTELVETRPAGDRTFQKWAAVVVPSGEEQRYTCHVQHEGLPKPLTLRWEP
C*01:02:01:01    WQWDGEDQTQDTELVETRPAGDGTFQKWAAVMVPSGEEQRYTCHVQHEGLPEPLTLRWEP
                 **.******************* ********:*******************:*******

As-Position      277                                                         336
A*01:01:01:01    SSQPTIPIVGIIAGLVLLGAV-ITGAVVAAVMWRRKSSDRKGGSYTQAASSDSAQGSDVS
B*07:02:01:01    SSQSTVPIVGIVAGLAVLAVV-VIGAVVAAVMCRRKSSGGKGGSYSQAACSDSAQGSDVS
C*01:02:01:01    SSQPTIPIVGIVAGLAVLAVLAVLGAVVAVVMCRRKSSGGKGGSCSQAASSNSAQGSDES
                 ***.*:*****:***.:*..: : *****.** *****. **** :***.*:****** *

As-Position      337
A*01:01:01:01    LTACKV
B*07:02:01:01    LTA---
C*01:02:01:01    LIACKA
                 * *
```

wherein A*01:01:01:01 is SEQ ID NO: 1, B*07:02:01:01 is SEQ ID NO: 2, and C*01:02:01:01 is SEQ ID NO: 3.

Fig. 7

Vector 1

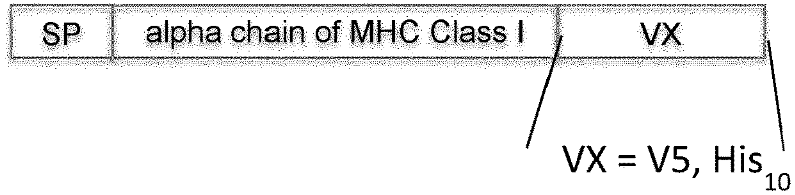

Vector 2

| SP | β2-m |
|---|---|

Fig. 8
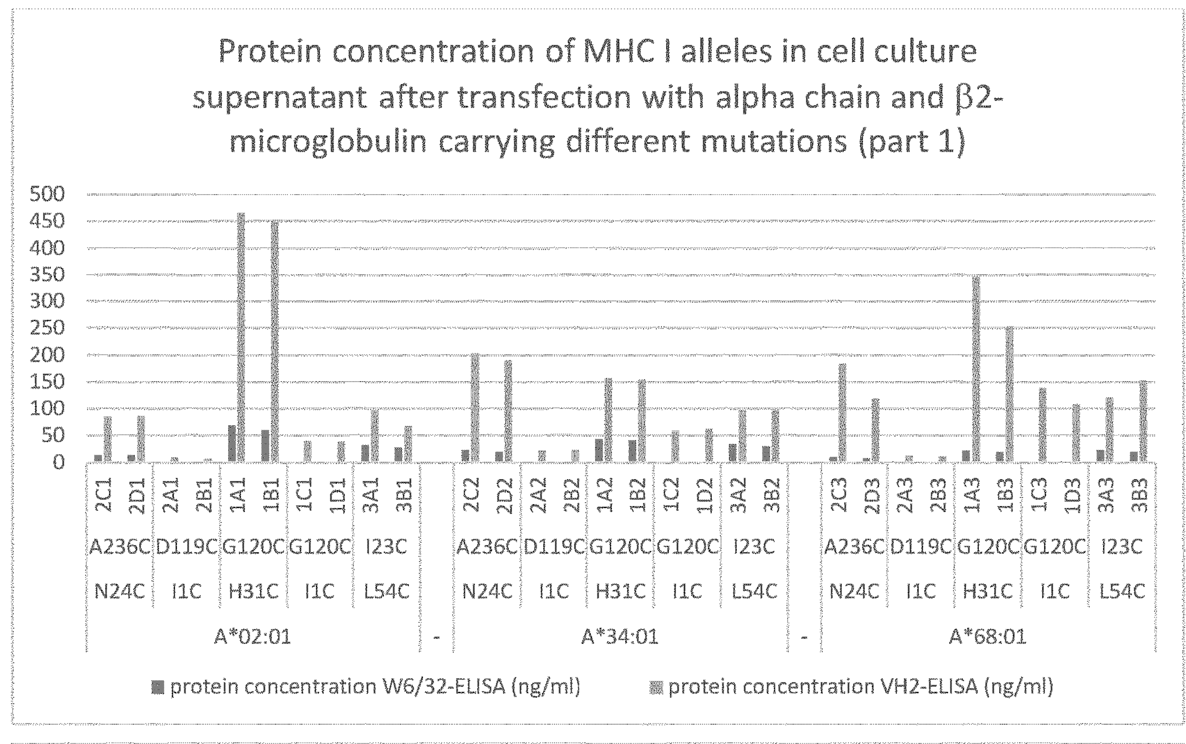
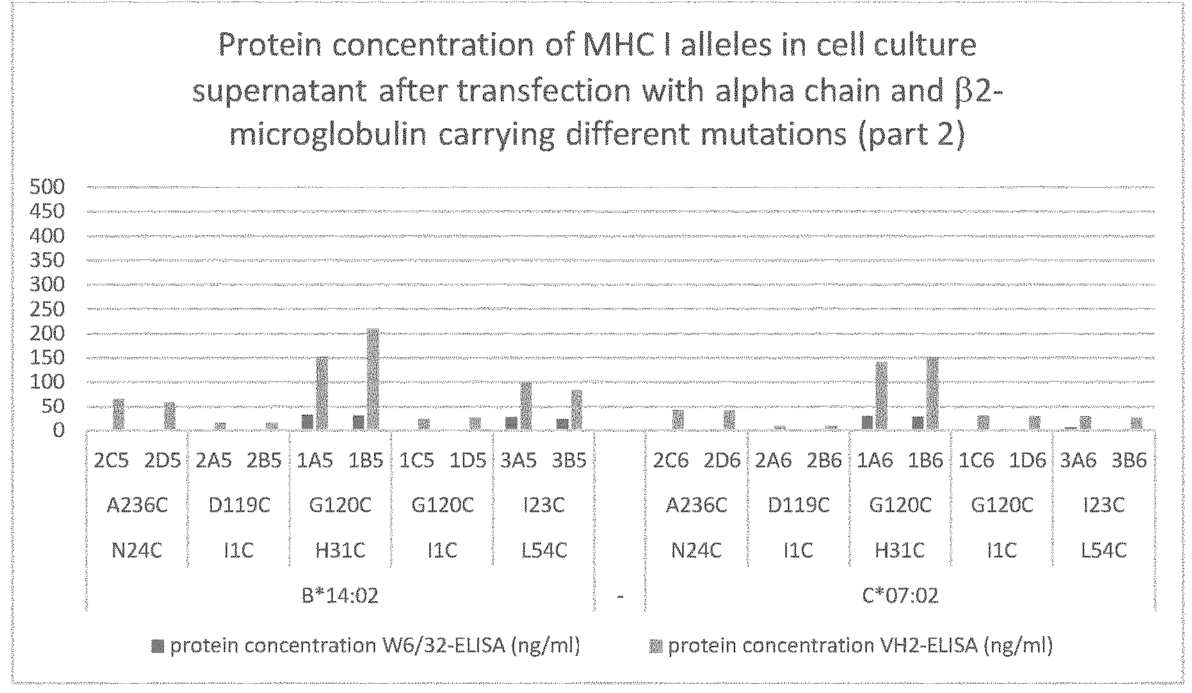

SEQUENCE LISTING

```
<160> NUMBER OF SEQ ID NOS: 78

<210> SEQ ID NO 1
<211> LENGTH: 341
<212> TYPE: PRT
<213> ORGANISM: Artificial Sequence
<220> FEATURE:
<223> OTHER INFORMATION: alpha chain of HLA A*01:01:01:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 1

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140
```

```
Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340
```

```
<210> SEQ ID NO 2
<211> LENGTH: 338
<212> TYPE: PRT
<213> ORGANISM: Artificial Sequence
<220> FEATURE:
<223> OTHER INFORMATION: alpha chain of HLA B*07:02:01:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
```

```
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 2

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala


<210> SEQ ID NO 3
<211> LENGTH: 342
<212> TYPE: PRT
```

```
<213> ORGANISM: Artificial Sequence
<220> FEATURE:
<223> OTHER INFORMATION: alpha chain of HLA C*01:02:01:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 3

Cys Ser His Ser Met Lys Tyr Phe Phe Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Trp Met Cys Gly Cys Asp Leu Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175
```

```
Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Met Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340


<210> SEQ ID NO 4
<211> LENGTH: 99
<212> TYPE: PRT
<213> ORGANISM: Artificial Sequence
<220> FEATURE:
<221> NAME/KEY: MUTAGEN
<222> LOCATION: 1
<223> OTHER INFORMATION: amino acid optionally exchanged for Cystein
<220> FEATURE:
<223> OTHER INFORMATION: beta 2-microglobulin without signal peptide
<220> FEATURE:
<221> NAME/KEY: MUTAGEN
<222> LOCATION: 12
<223> OTHER INFORMATION: amino acid optionally exchanged for Cystein
<220> FEATURE:
<221> NAME/KEY: MUTAGEN
<222> LOCATION: 24
<223> OTHER INFORMATION: amino acid optionally exchanged for Cystein
<220> FEATURE:
<221> NAME/KEY: MUTAGEN
<222> LOCATION: 31
<223> OTHER INFORMATION: amino acid optionally exchanged for Cystein
<220> FEATURE:
<221> NAME/KEY: MUTAGEN
<222> LOCATION: 53
<223> OTHER INFORMATION: amino acid optionally exchanged for Cystein
<220> FEATURE:
<221> NAME/KEY: MUTAGEN
<222> LOCATION: 54
<223> OTHER INFORMATION: amino acid optionally exchanged for Cystein
<220> FEATURE:
<221> NAME/KEY: MUTAGEN
<222> LOCATION: 55
<223> OTHER INFORMATION: amino acid optionally exchanged for Cystein
<220> FEATURE:
<221> NAME/KEY: MUTAGEN
<222> LOCATION: 98
<223> OTHER INFORMATION: amino acid optionally exchanged for Cystein

<400> SEQUENCE: 4

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
```

```
        20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 5
<211> LENGTH: 24
<212> TYPE: PRT
<213> ORGANISM: Artificial Sequence
<220> FEATURE:
<223> OTHER INFORMATION: signal peptide of HLA A*01:01:01:01

<400> SEQUENCE: 5

Met Ala Val Met Ala Pro Arg Thr Leu Leu Leu Leu Leu Ser Gly Ala
1               5                   10                  15

Leu Ala Leu Thr Gln Thr Trp Ala
            20


<210> SEQ ID NO 6
<211> LENGTH: 24
<212> TYPE: PRT
<213> ORGANISM: Artificial Sequence
<220> FEATURE:
<223> OTHER INFORMATION: signal peptide of HLA B*07:02:01:01

<400> SEQUENCE: 6

Met Leu Val Met Ala Pro Arg Thr Val Leu Leu Leu Leu Ser Ala Ala
1               5                   10                  15

Leu Ala Leu Thr Glu Thr Trp Ala
            20


<210> SEQ ID NO 7
<211> LENGTH: 24
<212> TYPE: PRT
<213> ORGANISM: Artificial Sequence
<220> FEATURE:
<223> OTHER INFORMATION: signal peptide of HLA C*01:02:01:01

<400> SEQUENCE: 7

Met Arg Val Met Ala Pro Arg Thr Leu Ile Leu Leu Leu Ser Gly Ala
1               5                   10                  15

Leu Ala Leu Thr Glu Thr Trp Ala
            20


<210> SEQ ID NO 8
<211> LENGTH: 20
<212> TYPE: PRT
<213> ORGANISM: Artificial Sequence
<220> FEATURE:
<223> OTHER INFORMATION: signal sequence of beta 2-microglobulin

<400> SEQUENCE: 8

Met Ser Arg Ser Val Ala Leu Ala Val Leu Ala Leu Leu Ser Leu Ser
1               5                   10                  15

Gly Leu Glu Ala
            20
```

<210> SEQ ID NO 9
<211> LENGTH: 284
<212> TYPE: PRT
<213> ORGANISM: Artificial Sequence
<220> FEATURE:
<223> OTHER INFORMATION: alpha chain of B*55:01_G120C
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: G120C
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 9

```
Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110

His Asn Gln Leu Ala Tyr Asp Cys Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
```

```
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile
        275                 280


<210> SEQ ID NO 10
<211> LENGTH: 341
<212> TYPE: PRT
<213> ORGANISM: Homo sapiens
<220> FEATURE:
<223> OTHER INFORMATION: alpha chain of A*01:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 10

Gly Ser His Ser Met Arg Tyr Phe Phe Thr Ser Val Ser Arg Pro Gly
1               5                   10                  15
```

```
Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340
```

<210> SEQ ID NO 11
<211> LENGTH: 341
<212> TYPE: PRT
<213> ORGANISM: Homo sapiens
<220> FEATURE:
<223> OTHER INFORMATION: alpha chain of A*02:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:

<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 11

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240
```

```
Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340


<210> SEQ ID NO 12
<211> LENGTH: 341
<212> TYPE: PRT
<213> ORGANISM: Homo sapiens
<220> FEATURE:
<223> OTHER INFORMATION: alpha chain of A*03:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 12

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45
```

```
Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Ile Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Glu Ala Glu Gln Leu Arg Ala Tyr Leu
145                 150                 155                 160

Asp Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340
```

<210> SEQ ID NO 13
<211> LENGTH: 341
<212> TYPE: PRT
<213> ORGANISM: Homo sapiens
<220> FEATURE:
<223> OTHER INFORMATION: alpha chain of A*11:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN

```
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 13

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Ala Ala Glu Gln Gln Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270
```

```
Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340


<210> SEQ ID NO 14
<211> LENGTH: 341
<212> TYPE: PRT
<213> ORGANISM: Homo sapiens
<220> FEATURE:
<223> OTHER INFORMATION: alpha chain of A*23:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 14

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Glu Glu Thr
    50                  55                  60

Gly Lys Val Lys Ala His Ser Gln Thr Asp Arg Glu Asn Leu Arg Ile
```

```
65                  70                  75                  80

Ala Leu Arg Tyr Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Val His Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Asn Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340


<210> SEQ ID NO 15
<211> LENGTH: 341
<212> TYPE: PRT
<213> ORGANISM: Homo sapiens
<220> FEATURE:
<223> OTHER INFORMATION: alpha chain of A*24:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
```

```
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 15

Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Glu Glu Thr
    50                  55                  60

Gly Lys Val Lys Ala His Ser Gln Thr Asp Arg Glu Asn Leu Arg Ile
65                  70                  75                  80

Ala Leu Arg Tyr Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Ile Thr Lys
    130                 135                 140

Arg Lys Trp Glu Ala Ala His Val Ala Glu Gln Gln Arg Ala Tyr Leu
145                 150                 155                 160

Glu Gly Thr Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Val Pro Ile Val Gly Ile Ile
        275                 280                 285

Ala Gly Leu Val Leu Leu Gly Ala Val Ile Thr Gly Ala Val Val Ala
```

```
    290                 295                 300

Ala Val Met Trp Arg Arg Asn Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340


<210> SEQ ID NO 16
<211> LENGTH: 341
<212> TYPE: PRT
<213> ORGANISM: Homo sapiens
<220> FEATURE:
<223> OTHER INFORMATION: alpha chain of A*25:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 16

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Thr Asp Arg Glu Ser Leu Arg Ile
65                  70                  75                  80

Ala Leu Arg Tyr Tyr Asn Gln Ser Glu Asp Gly Ser His Thr Ile Gln
                85                  90                  95
```

```
Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Ala Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

<210> SEQ ID NO 17
<211> LENGTH: 341
<212> TYPE: PRT
<213> ORGANISM: Homo sapiens
<220> FEATURE:
<223> OTHER INFORMATION: alpha chain of A*26:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein

```
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 17

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Ala Gly Ala Val Val Ala
    290                 295                 300

Ala Val Met Trp Arg Arg Lys Ser Ser Asp Arg Lys Gly Gly Ser Tyr
305                 310                 315                 320
```

```
Ser Gln Ala Ala Ser Ser Asp Ser Ala Gln Gly Ser Asp Met Ser Leu
                325                 330                 335

Thr Ala Cys Lys Val
            340


<210> SEQ ID NO 18
<211> LENGTH: 341
<212> TYPE: PRT
<213> ORGANISM: Homo sapiens
<220> FEATURE:
<223> OTHER INFORMATION: alpha chain of A*29:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 18

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Leu Gln Thr
    50                  55                  60

Arg Asn Val Lys Ala Gln Ser Gln Thr Asp Arg Ala Asn Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys His Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125
```

```
Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

```
<210> SEQ ID NO 19
<211> LENGTH: 341
<212> TYPE: PRT
<213> ORGANISM: Artificial Sequence
<220> FEATURE:
<223> OTHER INFORMATION: alpha chain of A*30:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
```

```
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 19

Gly Ser His Ser Met Arg Tyr Phe Ser Thr Ser Val Ser Arg Pro Gly
1               5                   10                  15

Ser Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Arg Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Ile Met Tyr Gly Cys Asp Val Gly Ser Asp Gly Arg Phe Leu Arg Gly
            100                 105                 110

Tyr Glu Gln His Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Trp Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340
```

```
<210> SEQ ID NO 20
<211> LENGTH: 341
<212> TYPE: PRT
<213> ORGANISM: Artificial Sequence
<220> FEATURE:
<223> OTHER INFORMATION: alpha chain of A*31:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 20

Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Arg Pro Glu Tyr Trp Asp Gln Glu Thr
    50                  55                  60

Arg Asn Val Lys Ala His Ser Gln Ile Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
```

-continued

```
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340


<210> SEQ ID NO 21
<211> LENGTH: 341
<212> TYPE: PRT
<213> ORGANISM: Artificial Sequence
<220> FEATURE:
<223> OTHER INFORMATION: alpha chain of A*32:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
```

```
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 21

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala His Ser Gln Thr Asp Arg Glu Ser Leu Arg Ile
65                  70                  75                  80

Ala Leu Arg Tyr Tyr Asn Gln Ser Glu Ala Gly Ser His Thr Ile Gln
                85                  90                  95

Met Met Tyr Gly Cys Asp Val Gly Pro Asp Gly Arg Leu Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Met Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340


<210> SEQ ID NO 22
<211> LENGTH: 341
<212> TYPE: PRT
```

<213> ORGANISM: Artificial Sequence
<220> FEATURE:
<223> OTHER INFORMATION: alpha chain of A*33:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 22

```
Gly Ser His Ser Met Arg Tyr Phe Thr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala His Ser Gln Ile Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175
```

```
Glu Thr Leu Gln Arg Thr Asp Pro Pro Arg Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

<210> SEQ ID NO 23
<211> LENGTH: 341
<212> TYPE: PRT
<213> ORGANISM: Artificial Sequence
<220> FEATURE:
<223> OTHER INFORMATION: alpha chain of A*34:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244

<223> OTHER INFORMATION: amino acid optionally exchanged for Cystein

<400> SEQUENCE: 23

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Lys Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Leu
        275                 280                 285

Ala Gly Leu Val Leu Phe Gly Ala Val Ile Ala Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

<210> SEQ ID NO 24
<211> LENGTH: 341
<212> TYPE: PRT
<213> ORGANISM: Artificial Sequence
<220> FEATURE:
<223> OTHER INFORMATION: alpha chain of A*36:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 24

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Val His Ala Ala Glu Gln Arg Arg Val Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205
```

```
Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340


<210> SEQ ID NO 25
<211> LENGTH: 341
<212> TYPE: PRT
<213> ORGANISM: Artificial Sequence
<220> FEATURE:
<223> OTHER INFORMATION: alpha chain of A*43:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 25

Gly Ser His Ser Met Arg Tyr Phe Tyr Thr Ser Val Ser Arg Pro Gly
```

```
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Leu Gln Thr
    50                  55                  60

Arg Asn Val Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Ala Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

```
<210> SEQ ID NO 26
<211> LENGTH: 341
<212> TYPE: PRT
<213> ORGANISM: Artificial Sequence
<220> FEATURE:
<223> OTHER INFORMATION: alpha chain of A*66:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
```

<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 26

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Thr Ala His Glu Ala Glu Gln Trp Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
```

```
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Ala Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340


<210> SEQ ID NO 27
<211> LENGTH: 341
<212> TYPE: PRT
<213> ORGANISM: Artificial Sequence
<220> FEATURE:
<223> OTHER INFORMATION: alpha chain of A*68:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 27

Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30
```

```
Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Val Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340
```

<210> SEQ ID NO 28
<211> LENGTH: 341
<212> TYPE: PRT
<213> ORGANISM: Artificial Sequence
<220> FEATURE:
<223> OTHER INFORMATION: alpha chain of A*69:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 28

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Arg Asn Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255
```

```
Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340


<210> SEQ ID NO 29
<211> LENGTH: 341
<212> TYPE: PRT
<213> ORGANISM: Artificial Sequence
<220> FEATURE:
<223> OTHER INFORMATION: alpha chain of A*74:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 29

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60
```

```
Arg Asn Val Lys Ala His Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Pro Asp Gly Arg Leu Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ser Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Met Phe Ala Gly Ala Val Val Ala
    290                 295                 300

Ala Val Arg Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Met Ser Leu
                325                 330                 335

Thr Ala Cys Lys Val
            340
```

<210> SEQ ID NO 30
<211> LENGTH: 341
<212> TYPE: PRT
<213> ORGANISM: Artificial Sequence
<220> FEATURE:
<223> OTHER INFORMATION: alpha chain of A*80:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:

```
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 30

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Ser Gln
            20                  25                  30

Phe Val Gln Phe Asp Ser Asp Ala Ala Ser Gln Arg Met Glu Pro Arg
        35                  40                  45

Ala Pro Trp Ile Glu Gln Glu Glu Pro Glu Tyr Trp Asp Glu Glu Thr
    50                  55                  60

Arg Asn Val Lys Ala His Ser Gln Thr Asn Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Ala Arg Arg Ala Glu Gln Leu Arg Ala Tyr Leu
145                 150                 155                 160

Glu Gly Glu Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Lys Glu Lys Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Ile
        275                 280                 285
```

```
Ala Gly Leu Val Leu Leu Gly Ala Val Ile Ala Gly Ala Val Val Ala
    290                 295                 300

Ala Val Met Trp Arg Lys Lys Ser Ser Val Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340


<210> SEQ ID NO 31
<211> LENGTH: 338
<212> TYPE: PRT
<213> ORGANISM: Artificial Sequence
<220> FEATURE:
<223> OTHER INFORMATION: alpha chain of B*07:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 31

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
```

```
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

<210> SEQ ID NO 32
<211> LENGTH: 338
<212> TYPE: PRT
<213> ORGANISM: Artificial Sequence
<220> FEATURE:
<223> OTHER INFORMATION: alpha chain of B*08:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192

```
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 32

Gly Ser His Ser Met Arg Tyr Phe Asp Thr Ala Met Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320
```

```
Ser Gln Ala Ala Cys Ser Asp Ser Ala Gln Gly Ser Asp Val Ser Leu
                325                 330                 335

Thr Ala


<210> SEQ ID NO 33
<211> LENGTH: 338
<212> TYPE: PRT
<213> ORGANISM: Artificial Sequence
<220> FEATURE:
<223> OTHER INFORMATION: alpha chain of B*13:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 33

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Gln
            20                  25                  30

Phe Val Arg Phe Asp Ser Asp Ala Thr Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Leu Arg Tyr Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125
```

```
Asp Leu Ser Ser Trp Thr Ala Ala Asp Thr Ala Ala Gln Ile Thr Gln
    130                 135                 140

Leu Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

<210> SEQ ID NO 34
<211> LENGTH: 338
<212> TYPE: PRT
<213> ORGANISM: Artificial Sequence
<220> FEATURE:
<223> OTHER INFORMATION: alpha chain of B*14:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN

```
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 34

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Cys Lys Thr Asn Thr Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Trp Met Tyr Gly Cys Asp Val Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

```
<210> SEQ ID NO 35
<211> LENGTH: 338
<212> TYPE: PRT
<213> ORGANISM: Artificial Sequence
<220> FEATURE:
<223> OTHER INFORMATION: alpha chain of B*15:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 35

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160
```

```
Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 36
<211> LENGTH: 338
<212> TYPE: PRT
<213> ORGANISM: Artificial Sequence
<220> FEATURE:
<223> OTHER INFORMATION: alpha chain of B*18:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
```

```
<221> NAME/KEY: MUTAGEN
<222> LOCATION: 244
<223> OTHER INFORMATION: amino acid optionally exchanged for Cystein

<400> SEQUENCE: 36

Gly Ser His Ser Met Arg Tyr Phe His Thr Ser Val Ser Arg Pro Gly
1               5                   10                  15

Arg Gly Glu Pro Arg Phe Ile Ser Val Gly Tyr Val Asp Gly Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 37
<211> LENGTH: 338
<212> TYPE: PRT
<213> ORGANISM: Artificial Sequence
<220> FEATURE:
<223> OTHER INFORMATION: alpha chain of B*27:01
<220> FEATURE:
```

```
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 37

Gly Ser His Ser Met Arg Tyr Phe His Thr Ser Val Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
    50                  55                  60

Gln Ile Cys Lys Ala Lys Ala Gln Thr Tyr Arg Glu Asn Leu Arg Thr
65                  70                  75                  80

Ala Leu Arg Tyr Tyr Asn Gln Ser Glu Ala Gly Ser His Thr Leu Gln
                85                  90                  95

Asn Met Tyr Gly Cys Asp Val Gly Pro Asp Gly Arg Leu Leu Arg Gly
            100                 105                 110

Tyr His Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
```

```
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala


<210> SEQ ID NO 38
<211> LENGTH: 338
<212> TYPE: PRT
<213> ORGANISM: Artificial Sequence
<220> FEATURE:
<223> OTHER INFORMATION: alpha chain of B*35:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 38

Gly Ser His Ser Met Arg Tyr Phe Tyr Thr Ala Met Ser Arg Pro Gly
```

```
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 39
<211> LENGTH: 338
<212> TYPE: PRT
<213> ORGANISM: Artificial Sequence
<220> FEATURE:
<223> OTHER INFORMATION: alpha chain of B*37:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 39

```
Gly Ser His Ser Met Arg Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asp Leu Arg Thr
65                  70                  75                  80

Leu Leu Arg Tyr Tyr Asn Gln Ser Glu Ala Gly Ser His Thr Ile Gln
                85                  90                  95

Arg Met Ser Gly Cys Asp Val Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240
```

```
Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 40
<211> LENGTH: 338
<212> TYPE: PRT
<213> ORGANISM: Artificial Sequence
<220> FEATURE:
<223> OTHER INFORMATION: alpha chain of B*38:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 40

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45
```

```
Ala Pro Trp Ile Glu Gln Glu Gly Pro Glu Tyr Trp Asp Arg Asn Thr
    50                  55                  60

Gln Ile Cys Lys Thr Asn Thr Gln Thr Tyr Arg Glu Asn Leu Arg Ile
65                  70                  75                  80

Ala Leu Arg Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Thr Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

```
<210> SEQ ID NO 41
<211> LENGTH: 338
<212> TYPE: PRT
<213> ORGANISM: Artificial Sequence
<220> FEATURE:
<223> OTHER INFORMATION: alpha chain of B*39:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
```

```
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 41

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Cys Lys Thr Asn Thr Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Thr Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270
```

```
Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 42
<211> LENGTH: 338
<212> TYPE: PRT
<213> ORGANISM: Artificial Sequence
<220> FEATURE:
<223> OTHER INFORMATION: alpha chain of B*40:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 42

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80
```

```
Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Ser Gln
    130                 135                 140

Arg Lys Leu Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala


<210> SEQ ID NO 43
<211> LENGTH: 338
<212> TYPE: PRT
<213> ORGANISM: Artificial Sequence
<220> FEATURE:
<223> OTHER INFORMATION: alpha chain of B*41:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
```

```
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 43

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Trp Gln
                85                  90                  95

Arg Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
```

```
305                 310                 315                 320

Ser Gln Ala Ala Cys Ser Asp Ser Ala Gln Gly Ser Asp Val Ser Leu
                325                 330                 335

Thr Ala


<210> SEQ ID NO 44
<211> LENGTH: 338
<212> TYPE: PRT
<213> ORGANISM: Artificial Sequence
<220> FEATURE:
<223> OTHER INFORMATION: alpha chain of B*42:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 44

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
```

```
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Thr Cys Val Glu Trp Leu Arg Arg Tyr Leu Glu Asn Gly Lys
                165                 170                 175

Asp Thr Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

<210> SEQ ID NO 45
<211> LENGTH: 338
<212> TYPE: PRT
<213> ORGANISM: Artificial Sequence
<220> FEATURE:
<223> OTHER INFORMATION: alpha chain of B*44:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:

<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 45

```
Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Thr
65                  70                  75                  80

Ala Leu Arg Tyr Tyr Asn Gln Ser Glu Ala Gly Ser His Ile Ile Gln
                85                  90                  95

Arg Met Tyr Gly Cys Asp Val Gly Pro Asp Gly Arg Leu Leu Arg Gly
            100                 105                 110

Tyr Asp Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Val Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

```
<210> SEQ ID NO 46
<211> LENGTH: 338
<212> TYPE: PRT
<213> ORGANISM: Artificial Sequence
<220> FEATURE:
<223> OTHER INFORMATION: alpha chain of B*45:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 46

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Trp Gln
                85                  90                  95

Arg Met Tyr Gly Cys Asp Leu Gly Pro Asp Gly Arg Leu Leu Arg Gly
            100                 105                 110

Tyr Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160
```

```
Glu Gly Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 47
<211> LENGTH: 338
<212> TYPE: PRT
<213> ORGANISM: Artificial Sequence
<220> FEATURE:
<223> OTHER INFORMATION: alpha chain of B*46:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein

```
<220> FEATURE:
<221> NAME/KEY: MUTAGEN
<222> LOCATION: 244
<223> OTHER INFORMATION: amino acid optionally exchanged for Cystein

<400> SEQUENCE: 47

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Ala Pro Arg
        35                  40                  45

Ala Pro Trp Ile Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 48
<211> LENGTH: 338
<212> TYPE: PRT
<213> ORGANISM: Artificial Sequence
<220> FEATURE:
<223> OTHER INFORMATION: alpha chain of B*47:01
```

```
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 48

Gly Ser His Ser Met Arg Tyr Phe Tyr Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asp Leu Arg Thr
65                  70                  75                  80

Leu Leu Arg Tyr Tyr Asn Gln Ser Glu Ala Gly Ser His Thr Leu Gln
                85                  90                  95

Arg Met Phe Gly Cys Asp Val Gly Pro Asp Gly Arg Leu Leu Arg Gly
            100                 105                 110

Tyr His Gln Asp Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190
```

```
Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Val Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

<210> SEQ ID NO 49
<211> LENGTH: 338
<212> TYPE: PRT
<213> ORGANISM: Artificial Sequence
<220> FEATURE:
<223> OTHER INFORMATION: alpha chain of B*48:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 49

```
Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Ser Gln
    130                 135                 140

Arg Lys Leu Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Thr Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala
```

<210> SEQ ID NO 50
<211> LENGTH: 338
<212> TYPE: PRT
<213> ORGANISM: Artificial Sequence
<220> FEATURE:
<223> OTHER INFORMATION: alpha chain of B*49:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23

```
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 50

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Ile
65                  70                  75                  80

Ala Leu Arg Tyr Tyr Asn Gln Ser Glu Ala Gly Ser His Thr Trp Gln
                85                  90                  95

Arg Met Tyr Gly Cys Asp Leu Gly Pro Asp Gly Arg Leu Leu Arg Gly
            100                 105                 110

Tyr Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
```

```
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 51
<211> LENGTH: 338
<212> TYPE: PRT
<213> ORGANISM: Artificial Sequence
<220> FEATURE:
<223> OTHER INFORMATION: alpha chain of B*50:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 51

Gly Ser His Ser Met Arg Tyr Phe His Thr Ala Met Ser Arg Pro Gly
1               5                   10                  15

Arg Gly Glu Pro Arg Phe Ile Thr Val Gly Tyr Val Asp Asp Thr Leu
            20                  25                  30

Phe Val Arg Phe Asp Ser Asp Ala Thr Ser Pro Arg Lys Glu Pro Arg
```

```
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Trp Gln
                85                  90                  95

Arg Met Tyr Gly Cys Asp Leu Gly Pro Asp Gly Arg Leu Leu Arg Gly
            100                 105                 110

Tyr Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 52
<211> LENGTH: 338
<212> TYPE: PRT
<213> ORGANISM: Artificial Sequence
<220> FEATURE:
<223> OTHER INFORMATION: alpha chain of B*51:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 52

```
Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Tyr Arg Glu Asn Leu Arg Ile
65                  70                  75                  80

Ala Leu Arg Tyr Tyr Asn Gln Ser Glu Ala Gly Ser His Thr Trp Gln
                85                  90                  95

Thr Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270
```

```
Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 53
<211> LENGTH: 338
<212> TYPE: PRT
<213> ORGANISM: Artificial Sequence
<220> FEATURE:
<223> OTHER INFORMATION: alpha chain of B*52:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 53

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Glu Thr
    50                  55                  60

Gln Ile Ser Lys Thr Asn Thr Gln Thr Tyr Arg Glu Asn Leu Arg Ile
65                  70                  75                  80
```

```
Ala Leu Arg Tyr Tyr Asn Gln Ser Glu Ala Gly Ser His Thr Trp Gln
                85                  90                  95

Thr Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 54
<211> LENGTH: 338
<212> TYPE: PRT
<213> ORGANISM: Artificial Sequence
<220> FEATURE:
<223> OTHER INFORMATION: alpha chain of B*53:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:

```
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 54

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Tyr Arg Glu Asn Leu Arg Ile
65                  70                  75                  80

Ala Leu Arg Tyr Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300
```

```
Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 55
<211> LENGTH: 338
<212> TYPE: PRT
<213> ORGANISM: Artificial Sequence
<220> FEATURE:
<223> OTHER INFORMATION: alpha chain of B*54:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 55

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110
```

```
His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 56
<211> LENGTH: 338
<212> TYPE: PRT
<213> ORGANISM: Artificial Sequence
<220> FEATURE:
<223> OTHER INFORMATION: alpha chain of B*55:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein

```
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 56

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

```
<210> SEQ ID NO 57
<211> LENGTH: 338
<212> TYPE: PRT
<213> ORGANISM: Artificial Sequence
<220> FEATURE:
<223> OTHER INFORMATION: alpha chain of B*56:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 57

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
```

```
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 58
<211> LENGTH: 338
<212> TYPE: PRT
<213> ORGANISM: Artificial Sequence
<220> FEATURE:
<223> OTHER INFORMATION: alpha chain of B*57:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
```

```
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 58

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Ala Pro Arg
        35                  40                  45

Ala Pro Trp Ile Glu Gln Glu Gly Pro Glu Tyr Trp Asp Gly Glu Thr
    50                  55                  60

Arg Asn Met Lys Ala Ser Ala Gln Thr Tyr Arg Glu Asn Leu Arg Ile
65                  70                  75                  80

Ala Leu Arg Tyr Tyr Asn Gln Ser Glu Ala Gly Ser His Ile Ile Gln
                85                  90                  95

Val Met Tyr Gly Cys Asp Val Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala


<210> SEQ ID NO 59
<211> LENGTH: 338
<212> TYPE: PRT
<213> ORGANISM: Artificial Sequence
<220> FEATURE:
```

<223> OTHER INFORMATION: alpha chain of B*58:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 59

```
Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Gly Glu Thr
    50                  55                  60

Arg Asn Met Lys Ala Ser Ala Gln Thr Tyr Arg Glu Asn Leu Arg Ile
65                  70                  75                  80

Ala Leu Arg Tyr Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asp Gln Ser Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190
```

```
Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 60
<211> LENGTH: 338
<212> TYPE: PRT
<213> ORGANISM: Artificial Sequence
<220> FEATURE:
<223> OTHER INFORMATION: alpha chain of B*59:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 60

```
Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Tyr Arg Glu Asn Leu Arg Ile
65                  70                  75                  80

Ala Leu Arg Tyr Tyr Asn Gln Ser Glu Ala Gly Ser His Thr Trp Gln
                85                  90                  95

Thr Met Tyr Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 61
<211> LENGTH: 338
<212> TYPE: PRT
<213> ORGANISM: Artificial Sequence
<220> FEATURE:
<223> OTHER INFORMATION: alpha chain of B*67:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 61

```
Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asn Gln Phe Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Leu Arg Thr Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220
```

```
Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala


<210> SEQ ID NO 62
<211> LENGTH: 338
<212> TYPE: PRT
<213> ORGANISM: Artificial Sequence
<220> FEATURE:
<223> OTHER INFORMATION: alpha chain of B*78:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 62

Gly Ser His Ser Met Arg Tyr Phe Tyr Thr Ala Met Ser Arg Pro Gly
1               5                   10                  15

Arg Gly Glu Pro Arg Phe Ile Ala Val Gly Tyr Val Asp Asp Thr Gln
            20                  25                  30
```

```
Phe Val Arg Phe Asp Ser Asp Ala Ala Ser Pro Arg Thr Glu Pro Arg
        35                  40                  45

Ala Pro Trp Ile Glu Gln Glu Gly Pro Glu Tyr Trp Asp Arg Asn Thr
    50                  55                  60

Gln Ile Phe Lys Thr Asn Thr Gln Thr Asp Arg Glu Ser Leu Arg Asn
65                  70                  75                  80

Leu Arg Gly Tyr Tyr Asn Gln Ser Glu Ala Gly Ser His Thr Trp Gln
                85                  90                  95

Thr Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg His Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 63
<211> LENGTH: 338
<212> TYPE: PRT
<213> ORGANISM: Artificial Sequence
<220> FEATURE:
<223> OTHER INFORMATION: alpha chain of B*81:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:

<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 63

```
Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asn Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Ser Gln
    130                 135                 140

Arg Lys Leu Glu Ala Ala Arg Val Ala Glu Gln Leu Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Thr Ala Val Val Val Pro Ser Gly Glu Glu Gln Arg
                245                 250                 255

Tyr Thr Cys His Val Gln His Glu Gly Leu Pro Lys Pro Leu Thr Leu
```

```
            260                 265                 270

Arg Trp Glu Pro Ser Ser Gln Ser Thr Val Pro Ile Val Gly Ile Val
        275                 280                 285

Ala Gly Leu Ala Val Leu Ala Val Val Val Ile Gly Ala Val Val Ala
    290                 295                 300

Ala Val Met Cys Arg Arg Lys Ser Ser Gly Gly Lys Gly Gly Ser Tyr
305                 310                 315                 320

Ser Gln Ala Ala Cys Ser Asp Ser Ala Gln Gly Ser Asp Val Ser Leu
                325                 330                 335

Thr Ala


<210> SEQ ID NO 64
<211> LENGTH: 338
<212> TYPE: PRT
<213> ORGANISM: Artificial Sequence
<220> FEATURE:
<223> OTHER INFORMATION: alpha chain of B*82:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 64

Gly Ser His Ser Met Arg Tyr Phe Tyr Thr Ala Met Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
```

```
65                  70                  75                  80

Leu Arg Gly Tyr Tyr Asn Gln Ser Glu Ala Gly Ser His Thr Leu Gln
                85                  90                  95

Arg Met Phe Gly Cys Asp Leu Gly Pro Asp Gly Arg Leu Leu Arg Gly
            100                 105                 110

His Asn Gln Leu Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Val Ala Glu Gln Asp Arg Ala Tyr Leu
145                 150                 155                 160

Glu Asp Leu Cys Val Glu Ser Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile Val Gly Ile Val
        275                 280                 285

Ala Gly Leu Ala Val Leu Ala Val Val Val Ile Gly Ala Val Val Ala
    290                 295                 300

Thr Val Met Cys Arg Arg Lys Ser Ser Gly Gly Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala
```

<210> SEQ ID NO 65
<211> LENGTH: 342
<212> TYPE: PRT
<213> ORGANISM: Artificial Sequence
<220> FEATURE:
<223> OTHER INFORMATION: alpha chain of C*01:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein

```
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 65

Cys Ser His Ser Met Lys Tyr Phe Phe Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Trp Met Cys Gly Cys Asp Leu Gly Pro Asp Gly Arg Leu Leu Arg Gly
            100                 105                 110

Tyr Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Met Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300
```

```
Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340


<210> SEQ ID NO 66
<211> LENGTH: 342
<212> TYPE: PRT
<213> ORGANISM: Artificial Sequence
<220> FEATURE:
<223> OTHER INFORMATION: alpha chain of C*02:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 66

Cys Ser His Ser Met Arg Tyr Phe Tyr Thr Ala Val Ser Arg Pro Ser
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Asn Leu Arg Lys
65                  70                  75                  80

Leu Arg Gly Tyr Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
```

```
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Glu Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Thr Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 67
<211> LENGTH: 342
<212> TYPE: PRT
<213> ORGANISM: Artificial Sequence
<220> FEATURE:
<223> OTHER INFORMATION: alpha chain of C*03:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:

```
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 67

Gly Ser His Ser Met Arg Tyr Phe Tyr Thr Ala Val Ser Arg Pro Gly
1               5                   10                  15

Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Ile Leu Gln
                85                  90                  95

Arg Met Tyr Gly Cys Asp Val Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Lys Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
```

```
            325                 330                 335

Leu Ile Ala Cys Lys Ala
            340


<210> SEQ ID NO 68
<211> LENGTH: 342
<212> TYPE: PRT
<213> ORGANISM: Artificial Sequence
<220> FEATURE:
<223> OTHER INFORMATION: alpha chain of C*04:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 68

Gly Ser His Ser Met Arg Tyr Phe Ser Thr Ser Val Ser Trp Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Glu Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Asn Leu Arg Lys
65                  70                  75                  80

Leu Arg Gly Tyr Tyr Asn Gln Ser Glu Asp Gly Ser His Thr Leu Gln
                85                  90                  95

Arg Met Phe Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125
```

```
Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Lys Pro Ser Ser Gln Pro Thr Ile Pro Ile Val Gly Ile Val
        275                 280                 285

Ala Gly Leu Ala Val Leu Ala Val Leu Ala Val Leu Gly Ala Met Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 69
<211> LENGTH: 342
<212> TYPE: PRT
<213> ORGANISM: Artificial Sequence
<220> FEATURE:
<223> OTHER INFORMATION: alpha chain of C*05:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN

```
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 69

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Gln Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Asn Leu Arg Lys
65                  70                  75                  80

Leu Arg Gly Tyr Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Arg Ser Trp Thr Ala Ala Asp Lys Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Lys Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Gly Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

```
<210> SEQ ID NO 70
<211> LENGTH: 342
<212> TYPE: PRT
<213> ORGANISM: Artificial Sequence
<220> FEATURE:
<223> OTHER INFORMATION: alpha chain of C*06:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 70

Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Asn Leu Arg Lys
65                  70                  75                  80

Leu Arg Gly Tyr Tyr Asn Gln Ser Glu Asp Gly Ser His Thr Leu Gln
                85                  90                  95

Trp Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160
```

```
Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 71
<211> LENGTH: 342
<212> TYPE: PRT
<213> ORGANISM: Artificial Sequence
<220> FEATURE:
<223> OTHER INFORMATION: alpha chain of C*07:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237

<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 71

Cys Ser His Ser Met Arg Tyr Phe Asp Thr Ala Val Ser Arg Pro Gly
1 5 10 15

Arg Gly Glu Pro Arg Phe Ile Ser Val Gly Tyr Val Asp Asp Thr Gln
20 25 30

Phe Val Arg Phe Asp Ser Asp Ala Ala Ser Pro Arg Gly Glu Pro Arg
35 40 45

Ala Pro Trp Val Glu Gln Glu Gly Pro Glu Tyr Trp Asp Arg Glu Thr
50 55 60

Gln Asn Tyr Lys Arg Gln Ala Gln Ala Asp Arg Val Ser Leu Arg Asn
65 70 75 80

Leu Arg Gly Tyr Tyr Asn Gln Ser Glu Asp Gly Ser His Thr Leu Gln
85 90 95

Arg Met Tyr Gly Cys Asp Leu Gly Pro Asp Gly Arg Leu Leu Arg Gly
100 105 110

Tyr Asp Gln Ser Ala Tyr Asp Gly Lys Asp Tyr Ile Ala Leu Asn Glu
115 120 125

Asp Leu Arg Ser Trp Thr Ala Ala Asp Thr Ala Ala Gln Ile Thr Gln
130 135 140

Arg Lys Leu Glu Ala Ala Arg Ala Ala Glu Gln Leu Arg Ala Tyr Leu
145 150 155 160

Glu Gly Thr Cys Val Glu Trp Leu Arg Arg Tyr Leu Glu Asn Gly Lys
165 170 175

Glu Thr Leu Gln Arg Ala Glu Pro Pro Lys Thr His Val Thr His His
180 185 190

Pro Leu Ser Asp His Glu Ala Thr Leu Arg Cys Trp Ala Leu Gly Phe
195 200 205

Tyr Pro Ala Glu Ile Thr Leu Thr Trp Gln Arg Asp Gly Glu Asp Gln
210 215 220

Thr Gln Asp Thr Glu Leu Val Glu Thr Arg Pro Ala Gly Asp Gly Thr
225 230 235 240

Phe Gln Lys Trp Ala Ala Val Val Val Pro Ser Gly Gln Glu Gln Arg
245 250 255

Tyr Thr Cys His Met Gln His Glu Gly Leu Gln Glu Pro Leu Thr Leu
260 265 270

Ser Trp Glu Pro Ser Ser Gln Pro Thr Ile Pro Ile Met Gly Ile Val
275 280 285

Ala Gly Leu Ala Val Leu Val Val Leu Ala Val Leu Gly Ala Val Val
290 295 300

Thr Ala Met Met Cys Arg Arg Lys Ser Ser Gly Gly Lys Gly Gly Ser
305 310 315 320

Cys Ser Gln Ala Ala Cys Ser Asn Ser Ala Gln Gly Ser Asp Glu Ser
325 330 335

Leu Ile Thr Cys Lys Ala
340

<210> SEQ ID NO 72
<211> LENGTH: 342
<212> TYPE: PRT
<213> ORGANISM: Artificial Sequence

```
<220> FEATURE:
<223> OTHER INFORMATION: alpha chain of C*08:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 72

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Gln Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Thr Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Lys Thr Leu Gln Arg Ala Glu His Pro Lys Thr His Val Thr His His
```

```
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Gly Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 73
<211> LENGTH: 342
<212> TYPE: PRT
<213> ORGANISM: Artificial Sequence
<220> FEATURE:
<223> OTHER INFORMATION: alpha chain of C*12:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 73

```
Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 74
<211> LENGTH: 342
<212> TYPE: PRT
<213> ORGANISM: Artificial Sequence
<220> FEATURE:
<223> OTHER INFORMATION: alpha chain of C*14:02
<220> FEATURE:
<221> NAME/KEY: MUTAGEN
<222> LOCATION: 10

```
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 74

Cys Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Trp Met Phe Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205
```

```
Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340


<210> SEQ ID NO 75
<211> LENGTH: 342
<212> TYPE: PRT
<213> ORGANISM: Artificial Sequence
<220> FEATURE:
<223> OTHER INFORMATION: alpha chain of C*15:02
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 75

Cys Ser His Ser Met Arg Tyr Phe Tyr Thr Ala Val Ser Arg Pro Gly
1               5                   10                  15
```

```
Arg Gly Glu Pro His Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Asn Tyr Lys Arg Gln Ala Gln Thr Asp Arg Val Asn Leu Arg Lys
65                  70                  75                  80

Leu Arg Gly Tyr Tyr Asn Gln Ser Glu Ala Gly Ser His Ile Ile Gln
                85                  90                  95

Arg Met Tyr Gly Cys Asp Leu Gly Pro Asp Gly Arg Leu Leu Arg Gly
            100                 105                 110

His Asp Gln Leu Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 76
<211> LENGTH: 342
<212> TYPE: PRT
<213> ORGANISM: Artificial Sequence
<220> FEATURE:
<223> OTHER INFORMATION: alpha chain of C*16:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein

```
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 76

Cys Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Thr Asp Arg Val Ser Leu Arg Asn
65                  70                  75                  80

Leu Arg Gly Tyr Tyr Asn Gln Ser Glu Ala Gly Ser His Thr Leu Gln
                85                  90                  95

Trp Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Ala Ala Glu Gln Gln Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Leu Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240
```

```
Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340


<210> SEQ ID NO 77
<211> LENGTH: 348
<212> TYPE: PRT
<213> ORGANISM: Artificial Sequence
<220> FEATURE:
<223> OTHER INFORMATION: alpha chain of C*17:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:
<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 77

Gly Ser His Ser Met Arg Tyr Phe Tyr Thr Ala Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Gly Glu Pro Arg
```

```
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Asn Leu Arg Lys
65                  70                  75                  80

Leu Arg Gly Tyr Tyr Asn Gln Ser Glu Ala Gly Ser His Thr Ile Gln
                85                  90                  95

Arg Met Tyr Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Ser Gln
    130                 135                 140

Arg Lys Leu Glu Ala Ala Arg Glu Ala Glu Gln Leu Arg Ala Tyr Leu
145                 150                 155                 160

Glu Gly Glu Cys Val Glu Trp Leu Arg Gly Tyr Leu Glu Asn Gly Lys
                165                 170                 175

Glu Thr Leu Gln Arg Ala Glu Arg Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Gln Glu Pro Cys Thr Leu
            260                 265                 270

Arg Trp Lys Pro Ser Ser Gln Pro Thr Ile Pro Asn Leu Gly Ile Val
        275                 280                 285

Ser Gly Pro Ala Val Leu Ala Val Leu Ala Val Leu Ala Val Leu Ala
    290                 295                 300

Val Leu Gly Ala Val Val Ala Ala Val Ile His Arg Arg Lys Ser Ser
305                 310                 315                 320

Gly Gly Lys Gly Gly Ser Cys Ser Gln Ala Ala Ser Ser Asn Ser Ala
                325                 330                 335

Gln Gly Ser Asp Glu Ser Leu Ile Ala Cys Lys Ala
            340                 345
```

<210> SEQ ID NO 78
<211> LENGTH: 342
<212> TYPE: PRT
<213> ORGANISM: Artificial Sequence
<220> FEATURE:
<223> OTHER INFORMATION: alpha chain of C*18:01
<220> FEATURE:
<221> NAME/KEY: MUTAGEN
<222> LOCATION: 10
<223> OTHER INFORMATION: amino acid optionally exchanged for Cystein
<220> FEATURE:
<221> NAME/KEY: MUTAGEN
<222> LOCATION: 23
<223> OTHER INFORMATION: amino acid optionally exchanged for Cystein
<220> FEATURE:
<221> NAME/KEY: MUTAGEN
<222> LOCATION: 35
<223> OTHER INFORMATION: amino acid optionally exchanged for Cystein
<220> FEATURE:

<221> NAME/KEY: MUTAGEN
<222> LOCATION: 119
<223> OTHER INFORMATION: amino acid optionally exchanged for Cystein
<220> FEATURE:
<221> NAME/KEY: MUTAGEN
<222> LOCATION: 120
<223> OTHER INFORMATION: amino acid optionally exchanged for Cystein
<220> FEATURE:
<221> NAME/KEY: MUTAGEN
<222> LOCATION: 192
<223> OTHER INFORMATION: amino acid optionally exchanged for Cystein
<220> FEATURE:
<221> NAME/KEY: MUTAGEN
<222> LOCATION: 231
<223> OTHER INFORMATION: amino acid optionally exchanged for Cystein
<220> FEATURE:
<221> NAME/KEY: MUTAGEN
<222> LOCATION: 236
<223> OTHER INFORMATION: amino acid optionally exchanged for Cystein
<220> FEATURE:
<221> NAME/KEY: MUTAGEN
<222> LOCATION: 237
<223> OTHER INFORMATION: amino acid optionally exchanged for Cystein
<220> FEATURE:
<221> NAME/KEY: MUTAGEN
<222> LOCATION: 244
<223> OTHER INFORMATION: amino acid optionally exchanged for Cystein

<400> SEQUENCE: 78

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
    50                  55                  60

Gln Lys Tyr Lys Arg Gln Ala Gln Ala Asp Arg Val Asn Leu Arg Lys
65                  70                  75                  80

Leu Arg Gly Tyr Tyr Asn Gln Ser Glu Asp Gly Ser His Thr Leu Gln
                85                  90                  95

Arg Met Phe Gly Cys Asp Leu Gly Pro Asp Gly Arg Leu Leu Arg Gly
            100                 105                 110

Tyr Asn Gln Phe Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Trp Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Thr Leu
```

```
            260                 265                 270

Arg Trp Lys Pro Ser Ser Gln Pro Thr Ile Pro Ile Val Gly Ile Val
        275                 280                 285

Ala Gly Leu Ala Val Leu Val Val Leu Ala Val Leu Gly Ala Val Val
    290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

STABILIZED MHC I

The present invention relates to modified MHC I molecules that can be expressed in cell culture and are more stable than natural MHC I molecules. Further, the invention relates to analytical processes using the modified MHC I molecules, e.g. for determination of antibodies in a serum sample directed against these MHC I molecules, or in tetramer staining. The MHC I molecules comprise or consist of a heavy chain (alpha chain) and a β2-microglobulin, wherein the alpha chain may be devoid of a transmembrane domain to give a soluble MHC I molecule, or a transmembrane domain may be linked to the C-terminus of the alpha chain, giving a MHC I molecule that is bound to a cell membrane, e.g. anchored in the membrane of the cell expressing the MHC I molecule. Accordingly, the stabilized MHC I molecules can be soluble or can be membrane-bound to a cell membrane.

The MHC I molecules of the invention have the advantage, e.g. in soluble form in which they have no transmembrane domain, that the alpha chain is stably associated with the β2-microglobulin also in the absence of a cognate antigen that has affinity to the antigen binding site of the alpha chain. The MHC I molecules of the invention can therefore preferably be produced in a state that is free from cognate antigen, e.g. free from antigen bound to the alpha chain. MHC I molecules of the invention which are devoid of cognate antigen bound to the alpha chain can e.g. be used for analytical processes in which the MHC I molecule is contacted with an antigen after synthesis of the MHC I molecule. An analytical process includes contacting an MHC I molecule according to the invention with a sample previously obtained from a patient, and preferably providing the result of the analytical process to the patient or to a medic appointed by the patient.

STATE OF THE ART

Shields et al., The Journal of Biological Chemistry 28010-28018 (1998) describes that exogenous β2-microglobulin, especially a S55V mutant of β2-microglobulin, stabilizes human cell surface MHC I molecules and facilitates their loading with peptides.

U.S. Pat. No. 6,682,741 B1 describes a mutant of the class I major histocompatibility complex protein (MHC I), which comprises a heavy chain (alpha chain) in association with a light chain β2-microglobulin), wherein compared to wild-type β2-microglobulin (S55) the mutation S55V in the β2-microglobulin confers higher stability to HLA-A1, HLA-A2 and HLA-A3 by a factor of 2 to 3 in the presence of a specific binding peptide and an appropriate HLA-specific antibody.

Amino acid sequences of MHC I molecules, especially of HLA I molecules are known and are available from the European Bioinformatics Institute, e.g. at https://ebi.ac.uk/ipd/imgt/hla/.

WO2017/201131 A1 describes an MHC I molecule that is covalently linked by a disulphide bond to a β2-microglobulin, which β2-microglobulin is fused to a peptide forming an epitope binding to the MHC I.

WO2019/051091 A1 describes an MHC I molecule that is covalently linked by a disulphide bond to a β2-microglobulin, wherein one of these is fused to a peptide forming an epitope binding to the MHC I.

OBJECT OF THE INVENTION

It is an object of the invention to provide alternative MHC I molecules which preferably in comparison to natural MHC I molecules have an increased stability, e.g. against dissociation. More preferably, the invention shall provide MHC I molecules which are stable, e.g. against dissociation, in the absence of a peptide or other molecule binding to the MHC I molecule, and which preferably is soluble, e.g. without a transmembrane domain. It is a further object to provide a process for producing MHC I molecules which are stable and free from a peptide or other molecule bound to the MHC I. A further object is to provide an analytical process which uses a stable MHC I molecule, which optionally has no antigen bound to the alpha chain, and which is soluble, e.g. without a transmembrane domain. The MHC I molecules of the invention shall be free from a covalently bound cognate antigenic peptide binding to the alpha chain bound by at least one disulphide bond to the β2-microglobulin.

DESCRIPTION OF THE INVENTION

Herein, the term major histocompatibility complex I (MHC I) includes the human leukocyte antigen I (HLA I), especially for proteins comprising or consisting of a heavy chain (alpha chain) of MHC I associated with a β2-microglobulin, which are e.g. available at https://ebi.ac.uk/ipd/imgt/hla/. Generally, the MHC I can be a HLA A, HLA B, or HLA C, or, less preferably, HLA E, HLA F, or HLA G. Preferably, the MHC I molecules have the amino acid sequence of a human MHC I molecule, but including the mutations resulting in the changes of amino acids to Cystein as described in the following.

The invention achieves the object by the features of the claims, especially by providing a MHC I which has at least one covalent bond formed between an Cystein in the alpha chain and an amino acid residue of the β2-microglobulin, and which preferably has at least one pair of Cystein residues, of which one is in the alpha chain and one is in the β2-microglobulin, which Cystein residues form a disulfide bond between the alpha chain and the β2-microglobulin. The bond formed between at least one pair of amino acids, one of which amino acids of the pair is a Cystein in the alpha chain and one of which amino acids of the pair is an amino acid having a group that is reactive with a thiol group, which amino acid is located in the β2-microglobulin.

The MHC I molecule of the invention specifically is free from a covalently bound peptide epitope that is a cognate antigen binding into the peptide binding cleft formed by the alpha chain that is bound by at least one disulphide bond to the β2-microglobulin. Accordingly, the MHC I molecule of the invention does not contain a cognate antigenic peptide that is linked to a terminus of the alpha chain or of the β2-microglobulin chain.

Accordingly, the MHC I molecule of the invention comprises or consists of an alpha chain and a β2-microglobulin which are linked by at least one disulfide bond formed between them, without a cognate antigenic peptide covalently bound to the MHC I molecule, and preferably without a transmembrane domain. As the MHC I molecule of the invention is devoid of a covalently bound antigenic peptide that could be bound by the MHC I molecule, e.g. the binding cleft of its alpha chain, only a free peptide, e.g. a separately solute peptide, to which the MHC I molecule has affinity, can be associated with the MHC I molecule, e.g. with the binding cleft of the alpha chain.

Generally herein, a cognate antigenic peptide is also referred to as antigen peptide or cognate antigen, and these terms define a peptide that has at least some affinity to the binding cleft of the MHC I molecule, especially to the binding cleft of the alpha chain of the MHC I molecule, when the alpha chain is associated with a β2-microglobulin. Preferably, the cognate antigenic peptide is defined as a peptide that has a dissociation constant ($K_D$) of 1 μM or lower. Determination of the dissociation constant preferably is in PBS buffer (7 mM NaH2PO4, 150 mM NaCl, pH 7.4) at 20° C. and/or at 37° C.

The MHC I molecules of the invention due to the disulfide bond between the alpha chain and the β2-microglobulin can have increased stability and still have a native MHC I conformation as determined by binding of W6/32 antibody, e.g. when lacking the transmembrane domain, in the absence or presence of an antigenic peptide arranged in the binding cleft of the alpha chain. This increased stability was e.g. found in comparison to wild-type MHC I lacking the transmembrane domain in SDS-PAGE under non-reducing conditions.

Further, certain of the MHC I molecules of the invention have the advantage of being stable, e.g. stable in solution when devoid of a transmembrane domain, when expressed in animal cells, especially in cultivated human cells, and allow for loading of the MHC I binding site with a soluble cognate antigen, e.g. replacing a peptide bound to the MHC I by a cognate antigen by adding the cognate antigen to the solution containing the MHC I molecule. During the preparation of the invention, it was found that some combinations of an alpha chain and a β2-microglobulin that contain Cysteines for forming disulphide bridges between these, devoid of cognate antigenic peptide fused to one of these, cannot be expressed in cultivated cells. For example, an MHC I consisting of an alpha chain of HLA I having a Cystein in amino acid position 119 in combination with a β2-microglobulin containing a Cystein in amino acid position 1 was found to be not expressed in functional conformation, as determined by binding of W6/32 antibody. As additional examples, an MHC I consisting of an alpha chain of HLA I having a Cystein in amino acid position 120 in combination with a β2-microglobulin containing a Cystein in amino acid position 3, an MHC I consisting of an alpha chain of HLA I having a Cystein in amino acid position 96 in combination with a β2-microglobulin containing a Cystein in amino acid position 31, an MHC I consisting of an alpha chain of HLA I having a Cystein in amino acid position 96 in combination with a β2-microglobulin containing a Cystein in amino acid position 60, and an MHC I consisting of an alpha chain of HLA I having a Cystein in amino acid position 234 in combination with a β2-microglobulin containing a Cystein in amino acid position 8 were found to be not expressed in functional conformation, as determined by binding of W6/32 antibody. Determination of the binding of W6/32 antibody preferably is in PBS buffer (7 mM NaH2PO4, 150 mM NaCl, pH 7.4) at 20° C. and/or at 37° C.

MHC I, especially human HLA I and murine MHC I are known, e.g. from https://www.ebi.ac.uk/ipd/imgt/hla/download.html), release 0.3.35, which can be downloaded from ftp://ftp.ebi.ac.uk/pub/databases/ipd/imgt/hla/ or from https://github.com/ANHIG/IMGTHLA/tree/Latest/alignments, showing the homology of MHC I, especially of its alpha chains. The alpha chain of MHC I, especially of HLA I, includes amino acid sequences having a sequence identity of at least 90%, at least 91%, at least 92%, at least 93%, at least 94%, preferably of at least 95%, e.g. at least 96% or at least 97% or at least 98% or at least 99% with one or more of SEQ ID NO: 1, SEQ ID NO: 2, SEQ ID NO: 3, SEQ ID NO: 9, or SEQ ID NO: 10 to SEQ ID NO: 78. SEQ ID NO: 10 to SEQ ID NO: 78 are the amino acid sequences of A*01:01, A*02:01, A*03:01, A*11:01, A*23:01, A*24:02, A*25:01, A*26:01, A*29:01, A*30:01, A*31:01, A*32:01, A*33:01, A*34:01, A*36:01, A*43:01, A*66:01, A*68:01, A*69:01, A*74:01, A*80:01, B*07:02, B*08:01, B*13:01, B*14:01, B*15:01, B*18:01, B*27:01, B*35:01, B*37:01, B*38:01, B*39:01, B*40:01, B*41:01, B*42:01, B*44:02, B*45:01, B*46:01, B*47:01, B*48:01, B*49:01, B*50:01, B*51:01, B*52:01, B*53:01, B*54:01, B*55:01, B*56:01, B*57:01, B*58:01, B*59:01, B*67:01, B*78:01, B*81:01, B*82:01, C*01:02, C*02:02, C*03:02, C*04:01, C*05:01, C*06:02, C*07:01, C*08:01, C*12:02, C*14:02, C*15:02, C*16:01, C*17:01, C*18:01, each without the N-terminal signal peptide. Generally herein, amino acid sequences are related to from their N-terminus to their C-terminus. Preferably, the alpha chain of MHC I may at least comprise or consist of amino acids No. 3 to 272 of the alpha chain, e.g. of SEQ ID NO: 1, SEQ ID NO: 2, SEQ ID NO: 3, SEQ ID NO: 9 or one of SEQ ID NO: 10 to SEQ ID NO: 78, which section of amino acids No. 3 to 272 can be determined to exclude its signal peptide, its transmembrane domain and/or its intracellular domain.

Optionally, the alpha chain may additionally contain one or more mutations contained in the group comprising or consisting of 74L, 223A, 224E, 225D, 226A, 227K, 229A, 245V (weakening or abolishing interaction with CD8), 227K and/or 228A, 139C and/or one of 84C and 85C (forming a disulfide bond within the alpha chain), and/or 115E.

The β2-microglobulin, especially the human or murine β2-microglobulin, includes amino acid sequences having a sequence identity of at least 90%, at least 91%, at least 92%, at least 93%, at least 94%, preferably of at least 95%, e.g. at least 96% or at least 97% or at least 98% with SEQ ID NO: 4.

The β2-microglobulin, especially the human or murine β2-microglobulin, may at least comprise or consist of amino acids No. 3 to 97 of the β2-microglobulin, determined excluding its signal peptide.

Optionally, the β2-microglobulin may additionally contain one or more mutations contained in the group comprising or consisting of K58E and/or S55V, with its amino acid sequence determined excluding its signal peptide.

For the β2-microglobulin, the Cystein residue that forms a covalent bond to a residue of the alpha chain can be replaced by another amino acid, which may be a natural or a synthetic amino acid, which carries a group that is reactive with the thiol group of the Cystein of the alpha chain. The Cystein of the alpha chain and the amino acid of the β2-microglobulin which form a bond between the alpha chain and the β2-microglobulin, are defined as pairs of amino acids in positions of the alpha chain and of the β2-microglobulin. In the β2-microglobulin the amino acid that carries a group which is reactive with a thiol group can e.g. be selected from a thiol group, a maleimide group, a iodoacetamide group, and an alkene group. The amino acid that carries a group which is reactive with a thiol group can e.g. be introduced into the β2-microglobulin by derivatisation of a Cystein or by chemical, e.g. non-ribosomal, synthesis of the β2-microglobulin using a natural or a synthetic amino acid in the respective position of the at least one pair of amino acids. Chemical synthesis of peptides is generally known, e.g. by solution using protective group chemistry, or by solid-phase synthesis, e.g. according to Merrifield and further developments of this method. In embodiments in which the β2-microglobulin is produced by derivatisation of a Cystein or by chemical, e.g. non-ribosomal synthesis, the β2-microglobulin can be associated with the alpha chain to produce an MHC I molecule in which at least one covalent bond formed between the pairs of amino acids connects the alpha chain and the β2-microglobulin.

Herein, the amino acid in the position of the β2-microglobulin which is part of the at least one pair of amino acids, is generally represented by Cystein. In an embodiment, in the β2-microglobulin, the representative Cystein of the pair of amino acids is therefore Cystein or another natural or artificial, i.e. non-natural, amino acid having a group that is reactive with the thiol group of the Cystein of the alpha chain. The amino acids forming a covalent bond between the alpha chain and the β2-microglobulin herein are identified as pairs of amino acids, and as pairs of amino acid positions.

The amino acid (AA) positions of the alpha chain have been found in HLA A, as exemplified by SEQ ID NO: 1 (A*01:01:01:01), in HLA B, as exemplified by SEQ ID NO: 2 (B*07:02:01:01), as well as in HLA C, as exemplified by SEQ ID NO: 3 (C*01:02:01:01). SEQ ID NO: 1, NO: 2, NO: 3, and SEQ ID NO: 10 to SEQ ID NO: 78 are given without the N-terminal signal peptide. FIG. 6 shows a sequence alignment of SEQ ID NO: 1, NO: 2, and NO: 3, indicating some of the amino acid positions that can be mutated to Cystein for forming a disulfide bond with a Cystein of the β2-microglobulin. Preferably, with reference to SEQ ID NO: 1 for the alpha chain and with reference to SEQ ID NO: 4 as an example for the β2-microglobulin (given without the N-terminal signal peptide), at least one of the following pairs of Cystein residues as given in the table below is contained in the MHC I.

The following table gives the positions of amino acids forming covalent bonds between the alpha chain and the β2-microglobulin, especially Cysteins forming pairs that each form a covalent bond, especially a disulfide bond between alpha chain and β2-microglobulin of MHC I, wherein the numbering refers to the AA position of the respective peptide chain without signal peptide. A preferred alpha chain has SEQ ID NO: 1, SEQ ID NO: 2, SEQ ID NO: 3, and more preferably has SEQ ID NO: 9, or one of SEQ ID NO: 10 to SEQ ID NO: 78, which are given without a signal peptide.

β2-microglobulin may be linked directly to the N-terminus of AA No. 1 of the β2-microglobulin, or may be linked with an intermediate spacer of 1 to 4 amino acids to the N-terminus of AA No. 1 of the β2-microglobulin. According to the invention, no antigenic peptide is covalently bound to the MHC I molecule, e.g. to its alpha chain or its β2-microglobulin.

The following alleles of HLA I contain a Cystein in position 120 (counted without the signal peptide) of the alpha chain: A*03:227, A*36:05, B*08:127, B*13:95, C*04:78, C*05:41 and C*07:144.

For example, in the alpha chain

- the Cystein in position No. 120 can be caused by a mutation resulting in G120C,
- the Cystein in position No. 35 can be caused by a mutation resulting in R35C or Q35C,
- the Cystein in position No. 119 can be caused by a mutation resulting in D119C
- the Cystein in position No. 236 can be caused by a mutation resulting in A236C,
- the Cystein in position No. 23 can be caused by a mutation resulting in I23C,
- the Cystein in position No. 10 can be caused by a mutation resulting in T10C,
- the Cystein in position No. 192 can be caused by a mutation resulting in H192C,
- the Cystein in position No. 237 can be caused by a mutation resulting in G237C,
- the Cystein in position No. 231 can be caused by a mutation resulting in V231C,
- the Cystein in position No. 244 can be caused by a mutation resulting in W244C.

For example, in the β2-microglobulin

- the Cystein in position No. 31 can be caused by a mutation resulting in H31C,
- the Cystein in position No. 1 can be caused by a mutation resulting in I1C,
- the Cystein in position No. 24 can be caused by a mutation resulting in N24C,

| Pair No. | Amino acid position of alpha chain, without signal peptide (e.g. SEQ ID NO: 9, SEQ ID NO: 1, SEQ ID NO: 2, SEQ ID NO: 3, or SEQ ID NO: 10 to SEQ ID NO: 78): | Amino acid position of β2-microglobulin, without signal peptide (e.g. SEQ ID NO: 4) |
|---|---|---|
| 1 | No. 120 | No. 31 |
| 2 | No. 120 | No. 1 |
| 3 | No. 35 | No. 53 |
| 4 | No. 119 | No. 31 |
| 5 | No. 236 | No. 24 |
| 6 | No. 236 | No. 12 |
| 7 | No. 237 | No. 24 |
| 8 | No. 237 | No. 12 |
| 9 | No. 23 | No. 54 |
| 10 | No. 10 | No. 54 |
| 11 | No. 120 | additional amino acid, preferably Cystein, N-terminally of AA position No. 1 |
| 12 | No. 192 | No. 98 |
| 13 | No. 23 | No. 55 |
| 14 | No. 10 | No. 55 |
| 15 | No. 231 | additional amino acid, preferably Cystein, preferably directly C-terminally of AA position No. 99 |
| 16 | No. 244 | additional amino acid, preferably Cystein, preferably directly C-terminally of AA position No. 99 |

The additional amino acid, which preferably is Cystein, which is arranged N-terminally of AA position No. 1 in the

- the Cystein in position No. 12 can be caused by a mutation resulting in R12C, the Cysteín in position No. 53 can be caused by a mutation resulting in D53C the Cystein in position No. 54 can be caused by a mutation resulting in L54C, the Cystein in position No. 55 can be caused by a mutation resulting in S55C, the Cystein in position No. 98 can be caused by a mutation resulting in D98C.

In an embodiment, the amino acid in position No. 31, in position No. 1, in position No. 24, in position No. 12, in position No. 53, in position No. 54, in position No. 55, and/or in position No. 98 can be an amino acid other than Cystein, which amino acid has a group that is reactive with a thiol group, forming a bond by at least one pair of amino acids.

Optionally, an amino acid having a group that is reactive with the thiol group can be present as an additional amino acid at the C-terminus of β2-microglobulin. Such an additional C-terminal amino acid that is reactive with a thiol group can form a bond with the Cystein of the alpha chain, especially with a Cystein at amino acid position No. 231 or 244 of the alpha chain.

Herein, especially in the following, sequences SEQ ID NO: 1, NO: 2, NO: 3, NO: 9 and NO: 10 to SEQ ID NO: 78, are simply designated and related to as the alpha chain.

Preferably, the MHC I molecule contains a Cystein in position No. 120 of the alpha chain and a Cystein in position No. 31 of SEQ ID NO: 4, resulting in pair No. 1, and/or the MHC I molecule contains a Cystein in position No. 119 of the alpha chain and a Cystein in position No. 31 of SEQ ID NO: 4, resulting in pair No. 4, and/or, less preferred, the MHC I molecule contains a Cystein in position No. 120 of the alpha chain and a Cystein in position No. 1 of SEQ ID NO: 4, resulting in pair No. 2, or also less preferred the MHC I molecule contains a Cystein in position No. 119 of the alpha chain and a Cystein in position No. 1 of SEQ ID NO: 4, resulting in pair No. 3, and/or the MHC I molecule contains a Cystein in position No. 236 of the alpha chain and a Cystein in position No. 24 of SEQ ID NO: 4, resulting in pair No. 5 or the MHC I molecule contains a Cystein in position No. 236 of the alpha chain and a Cystein in position No. 12 of SEQ ID NO: 4, resulting in pair No. 6, and/or the MHC I molecule contains a Cystein in position No. 237 of the alpha chain and a Cystein in position No. 24 of SEQ ID NO: 4, resulting in pair No. 7, or the MHC I molecule contains a Cystein in position No. 237 of the alpha chain and a Cystein in position No. 12 of SEQ ID NO: 4, resulting in pair No. 8, and/or the MHC I molecule contains a Cystein in position No. 23 of the alpha chain and a Cystein in position No. 54 of SEQ ID NO: 4, resulting in pair No. 9, and/or the MHC I molecule contains a Cystein in position No. 10 of the alpha chain and a Cystein in position No. 54 of SEQ ID NO: 4, resulting in pair No. 10, or the MHC I molecule contains a Cystein in position No. 120 of the alpha chain and an additional Cystein arranged N-terminally of amino acid (AA) No. 1, which additional N-terminal Cystein could also be referred to as position No. 0 of SEQ ID NO: 4, resulting in pair No. 11, and/or the MHC I molecule contains a Cystein in position No. 192 of the alpha chain and a Cystein in position No. 98 of SEQ ID NO: 4, resulting in pair No. 12, and/or the MHC I molecule contains a Cystein in position No. 23 of the alpha chain and a Cystein in position No. 55 of SEQ ID NO: 4, resulting in pair No. 13, and/or the MHC I molecule contains a Cystein in position No. 10 of the alpha chain and a Cystein in position No. 55 of SEQ ID NO: 4, resulting in pair No. 14, and/or the MHC I molecule contains a Cystein in position No. 231 of the alpha chain and a Cystein directly C-terminally to position No. 99 of SEQ ID NO: 4, resulting in pair No. 15, and/or the MHC I molecule contains a Cystein in position No. 244 of the alpha chain and a Cystein directly C-terminally to position No. 99 of SEQ ID NO: 4, resulting in pair No. 16.

The MHC I molecule of the invention can contain exactly one of these pairs of Cysteins forming a disulfide bond between the alpha chain and the β2-microglobulin, or more of these pairs, e.g. exactly two or more of these pairs of Cysteins forming a disulfide bond between the alpha chain and the β2-microglobulin.

Two pairs of Cysteins forming a disulfide bond between the alpha chain and the β2-microglobulin can e.g. be selected from combinations of one pair of the group consisting of pairs 1, 2, 3, 4, 9, 10, 11, 12, 13, 14, 15, and 16, and one pair of the group consisting of pairs 5, 6, 7, 8; or combinations of one pair of the group consisting of pairs 1, 2, 4, 5, 6, 7, 8, 11, 12, 15, and 16, and one pair of the group consisting of pairs 3, 9, 10, 13, 14; or combinations of one pair of the group consisting of pairs 3, 5, 6, 7, 8, 9, 10, 12, 13, 14, 15, and 16, and one pair of the group consisting of pairs 1, 2, 4, and 11.

Examples of combinations of two of these pairs are e.g. pair No. 1 and pair No. 5, or pair No. 1 and pair No. 6, or pair No. 1 and pair No. 7, or pair No. 1 and pair No. 8, or pair No. 2 and pair No. 5, or pair No. 2 and pair No. 6, or pair No. 2 and pair No. 7, or pair No. 2 and pair No. 8, or pair No. 3 and pair No. 5, or pair No. 3 and pair No. 6, or pair No. 3 and pair No. 7, or pair No. 3 and pair No. 8, or pair No. 4 and pair No. 5, or pair No. 4 and pair No. 6, or pair No. 4 and pair No. 7, or pair No. 4 and pair No. 8, or pair No. 11 and pair No. 5, or pair No. 11 and pair No. 6, or pair No. 11 and pair No. 7, or pair No. 11 and pair No. 8, or pair No. 12 and pair No. 5, or pair No. 12 and pair No. 6, or pair No. 12 and pair No. 7, or pair No. 12 and pair No. 8, or pair No. 9 and pair No. 5, or pair No. 9 and pair No. 6, or pair No. 9 and pair No. 7, or pair No. 9 and pair No. 8, or pair No. 10 and pair No. 5, or pair No. 10 and pair No. 6, or pair No. 10 and pair No. 7, or pair No. 10 and pair No. 8, or pair No. 13 and pair No. 5, or pair No. 13 and pair No. 6, or pair No. 13 and pair No. 7, or pair No. 13 and pair No. 8, or pair No. 14 and pair No. 5, or pair No. 14 and pair No. 6, or pair No. 14 and pair No. 7, or pair No. 14 and pair No. 8, or pair No. 15 and pair No. 5, or pair No. 15 and pair No. 6, or pair No. 15 and pair No. 7, or pair No. 15 and pair No. 8, or pair No. 16 and pair No. 5, or pair No. 16 and pair No. 6, or pair No. 16 and pair No. 7, or pair No. 16 and pair No. 8, or pair No. 1 and pair No. 12, or pair No. 2 and pair No. 12, or pair No. 4 and pair No. 12, or pair No. 5 and pair No. 12, or pair No. 6 and pair No. 12, or pair No. 7 and pair No. 12, or pair No. 8 and pair No. 12, or pair No. 9 and pair No. 12, or pair No. 10 and pair No. 12, or pair No. 11 and pair No. 12, or pair No. 13 and pair No. 12, or pair No. 14 and pair No. 12, or pair No. 1 and pair No. 15, or pair No. 2 and pair No. 15, or pair No. 4 and pair No. 15, or pair No. 5 and pair No. 15, or pair No. 6 and pair No. 15, or pair No. 7 and pair No. 15, or pair No. 8 and pair No. 15, or pair No. 9 and pair No. 15, or pair No. 10 and pair No. 15, or pair No. 11 and pair No. 15, or pair No. 13 and pair No. 15, or pair No. 14 and pair No. 15, or pair No. 1 and pair No. 16, or pair No. 2 and pair No. 16, or pair No. 4 and pair No. 16, or pair No. 5 and pair No. 16, or pair No. 6 and pair No. 16, or pair No. 7 and pair No. 16, or pair No. 8 and pair No. 16, or pair No. 9 and pair No. 16, or pair No. 10 and pair No. 16, or pair No. 11 and pair No. 16, or pair No. 13 and pair No. 16, or pair No. 14 and pair No. 16, or pair No. 1 and pair No. 9, or pair No. 2 and pair No. 9, or pair No. 4 and pair No. 9, or pair No. 11 and pair No. 9, or pair No. 1 and pair No. 10, or pair No. 2 and pair No. 10, or pair No. 4 and pair No. 10, or pair No. 11 and pair No. 10, or pair No. 1 and pair No. 13, or pair No. 2 and pair No. 13, or pair No. 4 and pair No. 13, or pair No. 11 and pair No. 13, or pair No. 1 and pair No. 14, or pair No. 2 and pair No. 14, or pair No. 4 and pair No. 14, or pair No. 11 and pair No. 14.

Optionally, the MHC I molecule of the invention can contain three of these pairs of Cysteins forming a disulfide bond between the alpha chain and the β2-microglobulin, preferably one pair of the group consisting of pairs 1, 2, 4, and 11, and/or one pair of the group consisting of pairs 5, 6, 7, 8, and/or one pair of the group consisting of pairs 3, 9, 10, 13, 14, and/or one pair of the group consisting of pairs 12, 15, and 16. These three pairs can e.g. be pair No. 1 and pair No. 5 and pair No. 3, or
pair No. 1 and pair No. 6 and pair No. 3, or
pair No. 1 and pair No. 7 and pair No. 3, or
pair No. 1 and pair No. 8 and pair No. 3, or
pair No. 2 and pair No. 5 and pair No. 3, or
pair No. 2 and pair No. 6 and pair No. 3, or
pair No. 2 and pair No. 7 and pair No. 3, or
pair No. 2 and pair No. 8 and pair No. 3, or
pair No. 4 and pair No. 5 and pair No. 3, or
pair No. 4 and pair No. 6 and pair No. 3, or
pair No. 4 and pair No. 7 and pair No. 3, or
pair No. 4 and pair No. 8 and pair No. 3, or
pair No. 11 and pair No. 5 and pair No. 3, or
pair No. 11 and pair No. 6 and pair No. 3, or
pair No. 11 and pair No. 7 and pair No. 3, or
pair No. 11 and pair No. 8 and pair No. 3, or
pair No. 1 and pair No. 5 and pair No. 9, or
pair No. 1 and pair No. 6 and pair No. 9, or
pair No. 1 and pair No. 7 and pair No. 9, or
pair No. 1 and pair No. 8 and pair No. 9, or
pair No. 2 and pair No. 5 and pair No. 9, or
pair No. 2 and pair No. 6 and pair No. 9, or
pair No. 2 and pair No. 7 and pair No. 9, or
pair No. 2 and pair No. 8 and pair No. 9, or
pair No. 4 and pair No. 5 and pair No. 9, or
pair No. 4 and pair No. 6 and pair No. 9, or
pair No. 4 and pair No. 7 and pair No. 9, or
pair No. 4 and pair No. 8 and pair No. 9, or
pair No. 11 and pair No. 5 and pair No. 9, or
pair No. 11 and pair No. 6 and pair No. 9, or
pair No. 11 and pair No. 7 and pair No. 9, or
pair No. 11 and pair No. 8 and pair No. 9, or
pair No. 12 and pair No. 5 and pair No. 9, or
pair No. 12 and pair No. 6 and pair No. 9, or
pair No. 12 and pair No. 7 and pair No. 9, or
pair No. 12 and pair No. 8 and pair No. 9, or
pair No. 1 and pair No. 5 and pair No. 10, or
pair No. 1 and pair No. 6 and pair No. 10, or
pair No. 1 and pair No. 7 and pair No. 10, or
pair No. 1 and pair No. 8 and pair No. 10, or
pair No. 2 and pair No. 5 and pair No. 10, or
pair No. 2 and pair No. 6 and pair No. 10, or
pair No. 2 and pair No. 7 and pair No. 10, or
pair No. 2 and pair No. 8 and pair No. 10, or
pair No. 4 and pair No. 5 and pair No. 10, or
pair No. 4 and pair No. 6 and pair No. 10, or
pair No. 4 and pair No. 7 and pair No. 10, or
pair No. 4 and pair No. 8 and pair No. 10, or
pair No. 11 and pair No. 5 and pair No. 10, or
pair No. 11 and pair No. 6 and pair No. 10, or
pair No. 11 and pair No. 7 and pair No. 10, or
pair No. 11 and pair No. 8 and pair No. 10, or
pair No. 12 and pair No. 5 and pair No. 10, or
pair No. 12 and pair No. 6 and pair No. 10, or
pair No. 12 and pair No. 7 and pair No. 10, or
pair No. 12 and pair No. 8 and pair No. 10, or
pair No. 1 and pair No. 5 and pair No. 13, or
pair No. 1 and pair No. 6 and pair No. 13, or
pair No. 1 and pair No. 7 and pair No. 13, or
pair No. 1 and pair No. 8 and pair No. 13, or
pair No. 2 and pair No. 5 and pair No. 13, or
pair No. 2 and pair No. 6 and pair No. 13, or
pair No. 2 and pair No. 7 and pair No. 13, or
pair No. 2 and pair No. 8 and pair No. 13, or
pair No. 4 and pair No. 5 and pair No. 13, or
pair No. 4 and pair No. 6 and pair No. 13, or
pair No. 4 and pair No. 7 and pair No. 13, or
pair No. 4 and pair No. 8 and pair No. 13, or
pair No. 11 and pair No. 5 and pair No. 13, or
pair No. 11 and pair No. 6 and pair No. 13, or
pair No. 11 and pair No. 7 and pair No. 13, or
pair No. 11 and pair No. 8 and pair No. 13, or
pair No. 1 and pair No. 5 and pair No. 14, or
pair No. 1 and pair No. 6 and pair No. 14, or
pair No. 1 and pair No. 7 and pair No. 14, or
pair No. 1 and pair No. 8 and pair No. 14, or
pair No. 2 and pair No. 5 and pair No. 14, or
pair No. 2 and pair No. 6 and pair No. 14, or
pair No. 2 and pair No. 7 and pair No. 14, or
pair No. 2 and pair No. 8 and pair No. 14, or
pair No. 4 and pair No. 5 and pair No. 14, or
pair No. 4 and pair No. 6 and pair No. 14, or
pair No. 4 and pair No. 7 and pair No. 14, or
pair No. 4 and pair No. 8 and pair No. 14, or
pair No. 11 and pair No. 5 and pair No. 14, or
pair No. 11 and pair No. 6 and pair No. 14, or
pair No. 11 and pair No. 7 and pair No. 14, or
pair No. 11 and pair No. 8 and pair No. 14, or
pair No. 1 and pair No. 5 and pair No. 12, or
pair No. 1 and pair No. 6 and pair No. 12, or
pair No. 1 and pair No. 7 and pair No. 12, or
pair No. 1 and pair No. 8 and pair No. 12, or
pair No. 2 and pair No. 5 and pair No. 12, or
pair No. 2 and pair No. 6 and pair No. 12, or
pair No. 2 and pair No. 7 and pair No. 12, or
pair No. 2 and pair No. 8 and pair No. 12, or
pair No. 4 and pair No. 5 and pair No. 12, or
pair No. 4 and pair No. 6 and pair No. 12, or
pair No. 4 and pair No. 7 and pair No. 12, or
pair No. 4 and pair No. 8 and pair No. 12, or
pair No. 11 and pair No. 5 and pair No. 12, or
pair No. 11 and pair No. 6 and pair No. 12, or
pair No. 11 and pair No. 7 and pair No. 12, or
pair No. 11 and pair No. 8 and pair No. 12, or
pair No. 1 and pair No. 5 and pair No. 15, or
pair No. 1 and pair No. 6 and pair No. 15, or
pair No. 1 and pair No. 7 and pair No. 15, or
pair No. 1 and pair No. 8 and pair No. 15, or
pair No. 2 and pair No. 5 and pair No. 15, or
pair No. 2 and pair No. 6 and pair No. 15, or pair No. 2 and pair No. 7 and pair No. 15, or
pair No. 2 and pair No. 8 and pair No. 15, or
pair No. 4 and pair No. 5 and pair No. 15, or
pair No. 4 and pair No. 6 and pair No. 15, or
pair No. 4 and pair No. 7 and pair No. 15, or
pair No. 4 and pair No. 8 and pair No. 15, or
pair No. 11 and pair No. 5 and pair No. 15, or
pair No. 11 and pair No. 6 and pair No. 15, or
pair No. 11 and pair No. 7 and pair No. 15, or
pair No. 11 and pair No. 8 and pair No. 15, or
pair No. 1 and pair No. 5 and pair No. 16, or
pair No. 1 and pair No. 6 and pair No. 16, or
pair No. 1 and pair No. 7 and pair No. 16, or
pair No. 1 and pair No. 8 and pair No. 16, or
pair No. 2 and pair No. 5 and pair No. 16, or
pair No. 2 and pair No. 6 and pair No. 16, or
pair No. 2 and pair No. 7 and pair No. 16, or
pair No. 2 and pair No. 8 and pair No. 16, or
pair No. 4 and pair No. 5 and pair No. 16, or
pair No. 4 and pair No. 6 and pair No. 16, or
pair No. 4 and pair No. 7 and pair No. 16, or
pair No. 4 and pair No. 8 and pair No. 16, or
pair No. 11 and pair No. 5 and pair No. 16, or
pair No. 11 and pair No. 6 and pair No. 16, or
pair No. 11 and pair No. 7 and pair No. 16, or
pair No. 11 and pair No. 8 and pair No. 16, or
pair No. 1 and pair No. 12 and pair No. 3, or
pair No. 1 and pair No. 15 and pair No. 3, or
pair No. 1 and pair No. 16 and pair No. 3, or
pair No. 2 and pair No. 12 and pair No. 3, or
pair No. 2 and pair No. 15 and pair No. 3, or
pair No. 2 and pair No. 16 and pair No. 3, or
pair No. 4 and pair No. 12 and pair No. 3, or
pair No. 4 and pair No. 15 and pair No. 3, or
pair No. 4 and pair No. 16 and pair No. 3, or
pair No. 11 and pair No. 12 and pair No. 3, or
pair No. 11 and pair No. 15 and pair No. 3, or
pair No. 11 and pair No. 16 and pair No. 3, or
pair No. 1 and pair No. 12 and pair No. 9, or
pair No. 1 and pair No. 15 and pair No. 9, or
pair No. 1 and pair No. 16 and pair No. 9, or
pair No. 2 and pair No. 12 and pair No. 9, or
pair No. 2 and pair No. 15 and pair No. 9, or
pair No. 2 and pair No. 16 and pair No. 9, or
pair No. 4 and pair No. 12 and pair No. 9, or
pair No. 4 and pair No. 15 and pair No. 9, or
pair No. 4 and pair No. 16 and pair No. 9, or
pair No. 11 and pair No. 12 and pair No. 9, or
pair No. 11 and pair No. 15 and pair No. 9, or
pair No. 11 and pair No. 16 and pair No. 9, or
pair No. 1 and pair No. 12 and pair No. 10, or
pair No. 1 and pair No. 15 and pair No. 10, or
pair No. 1 and pair No. 16 and pair No. 10, or
pair No. 2 and pair No. 12 and pair No. 10, or
pair No. 2 and pair No. 15 and pair No. 10, or
pair No. 2 and pair No. 16 and pair No. 10, or
pair No. 4 and pair No. 12 and pair No. 10, or
pair No. 4 and pair No. 15 and pair No. 10, or
pair No. 4 and pair No. 16 and pair No. 10, or
pair No. 11 and pair No. 12 and pair No. 10, or
pair No. 11 and pair No. 15 and pair No. 10, or
pair No. 11 and pair No. 16 and pair No. 10, or
pair No. 1 and pair No. 12 and pair No. 13, or
pair No. 1 and pair No. 15 and pair No. 13, or
pair No. 1 and pair No. 16 and pair No. 13, or
pair No. 2 and pair No. 12 and pair No. 13, or
pair No. 2 and pair No. 15 and pair No. 13, or
pair No. 2 and pair No. 16 and pair No. 13, or
pair No. 4 and pair No. 12 and pair No. 13, or
pair No. 4 and pair No. 15 and pair No. 13, or
pair No. 4 and pair No. 16 and pair No. 13, or
pair No. 11 and pair No. 12 and pair No. 13, or
pair No. 11 and pair No. 15 and pair No. 13, or
pair No. 11 and pair No. 16 and pair No. 13, or
pair No. 1 and pair No. 12 and pair No. 14, or
pair No. 1 and pair No. 15 and pair No. 14, or
pair No. 1 and pair No. 16 and pair No. 14, or
pair No. 2 and pair No. 12 and pair No. 14, or
pair No. 2 and pair No. 15 and pair No. 14, or
pair No. 2 and pair No. 16 and pair No. 14, or
pair No. 4 and pair No. 12 and pair No. 14, or
pair No. 4 and pair No. 15 and pair No. 14, or
pair No. 4 and pair No. 16 and pair No. 14, or
pair No. 11 and pair No. 12 and pair No. 14, or
pair No. 11 and pair No. 15 and pair No. 14, or
pair No. 11 and pair No. 16 and pair No. 14, or
pair No. 5 and pair No. 12 and pair No. 3, or
pair No. 5 and pair No. 15 and pair No. 3, or
pair No. 5 and pair No. 16 and pair No. 3, or
pair No. 5 and pair No. 12 and pair No. 9, or
pair No. 5 and pair No. 15 and pair No. 9, or
pair No. 5 and pair No. 16 and pair No. 9, or
pair No. 5 and pair No. 12 and pair No. 10, or
pair No. 5 and pair No. 15 and pair No. 10, or
pair No. 5 and pair No. 16 and pair No. 10, or
pair No. 5 and pair No. 12 and pair No. 13, or
pair No. 5 and pair No. 15 and pair No. 13, or
pair No. 5 and pair No. 16 and pair No. 13, or
pair No. 5 and pair No. 12 and pair No. 14, or
pair No. 5 and pair No. 15 and pair No. 14, or
pair No. 5 and pair No. 16 and pair No. 14, or
pair No. 6 and pair No. 12 and pair No. 3, or
pair No. 6 and pair No. 15 and pair No. 3, or
pair No. 6 and pair No. 16 and pair No. 3, or
pair No. 6 and pair No. 12 and pair No. 9, or
pair No. 6 and pair No. 15 and pair No. 9, or
pair No. 6 and pair No. 16 and pair No. 9, or
pair No. 6 and pair No. 12 and pair No. 10, or
pair No. 6 and pair No. 15 and pair No. 10, or
pair No. 6 and pair No. 16 and pair No. 10, or
pair No. 6 and pair No. 12 and pair No. 13, or
pair No. 6 and pair No. 15 and pair No. 13, or
pair No. 6 and pair No. 16 and pair No. 13, or
pair No. 6 and pair No. 12 and pair No. 14, or
pair No. 6 and pair No. 15 and pair No. 14, or
pair No. 6 and pair No. 16 and pair No. 14, or
pair No. 7 and pair No. 12 and pair No. 3, or
pair No. 7 and pair No. 15 and pair No. 3, or
pair No. 7 and pair No. 16 and pair No. 3, or
pair No. 7 and pair No. 12 and pair No. 9, or
pair No. 7 and pair No. 15 and pair No. 9, or
pair No. 7 and pair No. 16 and pair No. 9, or
pair No. 7 and pair No. 12 and pair No. 10, or
pair No. 7 and pair No. 15 and pair No. 10, or
pair No. 7 and pair No. 16 and pair No. 10, or
pair No. 7 and pair No. 12 and pair No. 13, or
pair No. 7 and pair No. 15 and pair No. 13, or
pair No. 7 and pair No. 16 and pair No. 13, or
pair No. 7 and pair No. 12 and pair No. 14, or
pair No. 7 and pair No. 15 and pair No. 14, or
pair No. 7 and pair No. 16 and pair No. 14, or
pair No. 8 and pair No. 12 and pair No. 3, or
pair No. 8 and pair No. 15 and pair No. 3, or
pair No. 8 and pair No. 16 and pair No. 3, or pair No. 8 and pair No. 12 and pair No. 9, or
pair No. 8 and pair No. 15 and pair No. 9, or
pair No. 8 and pair No. 16 and pair No. 9, or
pair No. 8 and pair No. 12 and pair No. 10, or
pair No. 8 and pair No. 15 and pair No. 10, or
pair No. 8 and pair No. 16 and pair No. 10, or
pair No. 8 and pair No. 12 and pair No. 13, or
pair No. 8 and pair No. 15 and pair No. 13, or
pair No. 8 and pair No. 16 and pair No. 13, or
pair No. 8 and pair No. 12 and pair No. 14, or
pair No. 8 and pair No. 15 and pair No. 14, or
pair No. 8 and pair No. 16 and pair No. 14.

Generally, as an option, the β2-microglobulin can comprise a mutation resulting in an S55V amino acid exchange as an additional mutation.

Preferably, the alpha chain contains a signal peptide sequence directly adjacent to the N-terminus the alpha chain, e.g. at the N-terminus of amino acid No. 1 of SEQ ID NO: 1, SEQ ID NO: 2, or SEQ ID NO: 3, or one of SEQ ID NO: 10 to SEQ ID NO: 78.

Preferably, the β2-microglobulin contains a signal peptide sequence directly adjacent to its N-terminus, or in case of an additional Cystein arranged at the N-terminus of the β2-microglobulin (e.g. pair No. 11 or No. 12) a signal peptide sequence at the N-terminus of the Cystein bound to the N-terminus of the β2-microglobulin.

It was found that the MHC I molecules of the invention can be expressed in eukaryotic cells, preferably in mammalian cells or insect cells or yeast or fungal cells, with the disulfide bonds formed between the Cystein residues formed by the pairs of Cystein residues.

It is an advantage of MHC I molecules according to the invention that they are stable to dissociation also in the absence of a cognate antigen binding to the alpha chain of the MHC I, wherein the MHC I can be composed of its alpha chain and β2-microglobulin. Therefore, the invention preferably allows the expression of the MHC I molecules in the absence of peptide or other molecule binding to the MHC I for production of the MHC I molecule without a peptide or other molecule bound to the binding groove of the alpha chain, alternatively, the MHC I molecules may be expressed with a peptide binding to its binding groove, followed by removing the bound peptide, e.g. by heating for dissociating the peptide from the binding groove of the MHC I, optionally followed by separating the peptide, e.g. by chromatography. Herein, a peptide or other molecule binding to the MHC I, especially to the alpha chain of MHC I, is also termed cognate antigen.

Generally preferred, MHC I molecules of the invention can be produced by expression from nucleic acid sequences encoding the MHC I molecule in mammalian cell culture, in insect cell culture, or in another eukaryotic cell culture, e.g. yeast or in a fungus. Optionally, the cell expressing the MHC I molecule and the culture, e.g. cultivating medium, does not contain a cognate antigen binding to the MHC I molecule, e.g. when expressing the MHC I molecule in yeast. Alternatively, the MHC I molecules can be expressed in a prokaryote, i.e. in a bacterium, both the alpha chain and the β2-microglobulin together in one bacterial cell or in separate bacterial cells, e.g. in separate bacterial cultures, followed by isolation of the alpha chain and the β2-microglobulin of the MHC I molecules, e.g. as inclusion bodies, respectively of the separate alpha chain and β2-microglobulin, with subsequent re-folding of the alpha chain and the β2-microglobulin combined to form MHC I molecules having the disulfide bond or binds, and separation of these molecules from other protein associates, e.g. from denatured single alpha chain or denatured β2-microglobulin or from multimers. For expression of MHC I molecules in bacterial cells, it is preferred that the alpha chain is devoid of a transmembrane domain.

The MHC I molecules of the invention preferably have a conformation that is considered close to or essentially identical to the natural conformation of natural MHC I consisting of alpha chain, β2-microglobulin in association with an antigen bound to the alpha chain. This natural conformation of the MHC I molecules of the invention is e.g. shown by the binding of W6/32 antibody to these MHC I molecules.

MHC I molecules of the invention can be expressed from a first expression cassette encoding the alpha chain and a separate second expression cassette encoding the β2-microglobulin. Optionally, MHC I molecules of the invention are expressed from one expression cassette under the control of one promoter, the expression cassette containing a coding sequence, from 5'-terminus to 3'-terminus for an optional first signal peptide—alpha chain—optional tag sequence—ribosomal skip sequence—optional second signal peptide—β2-microglobulin. The ribosomal skip sequence enables the production of the alpha chain and of the β2-microglobulin as separate peptides in close proximity, the close proximity including proximity of translation of the peptides both in time and localisation. Further, the ribosomal skip sequence preferably results in the stoichiometric expression of the alpha chain and of the β2-microglobulin as two separate proteins.

The MHC I molecules of the invention can be expressed from separate expression cassettes contained in one cell. This indicates that the alpha chain and the β2-microglobulin, when expressed from separate expression cassettes, combine to a complete MHC I molecule, e.g. in the endoplasmatic reticulum.

The optional first signal peptide preferably is a secretion signal peptide sequence, which is preferably directly linked to the N-terminus of the alpha chain, and which may e.g. be selected from natural signal peptides of MHC I molecules. Examples of suitable signal peptide sequences originating from alpha chains of natural HLA molecules are given as SEQ ID NO: 5, SEQ ID NO: 6, and SEQ ID NO: 7.

The optional second signal peptide preferably is a secretion signal peptide sequence, which is preferably directly linked to the N-terminus of the β2-microglobulin. A signal peptide of the human β2-microglobulin is given as SEQ ID NO: 8. The second signal peptide may have the same amino acid sequence as the first signal peptide.

The optional tag sequence may be selected from the V5 tag, streptavidin binding peptide (SBP) tag, and/or His tag, e.g. $His_{10}$ tag.

The ribosomal skip sequence may be the 2A sequence of porcine teschovirus-1 (P2A), the 2A sequence of Thoseaasigna virus (T2A), the 2A sequence of equine rhinitis A virus (ERAV), or the 2A sequence of foot-and-mouth-disease virus (FMDV).

Figure 5:
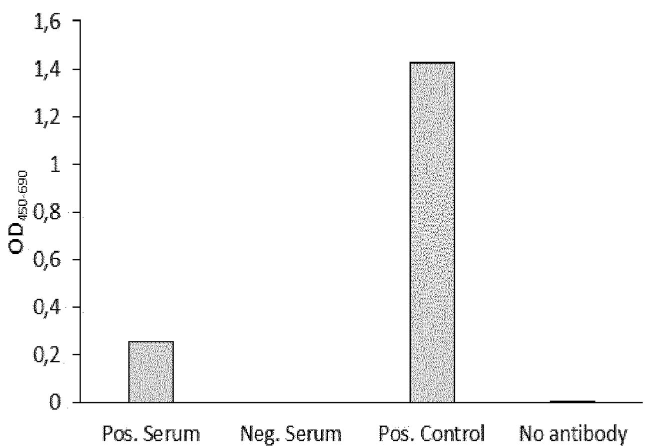
Figure 9:
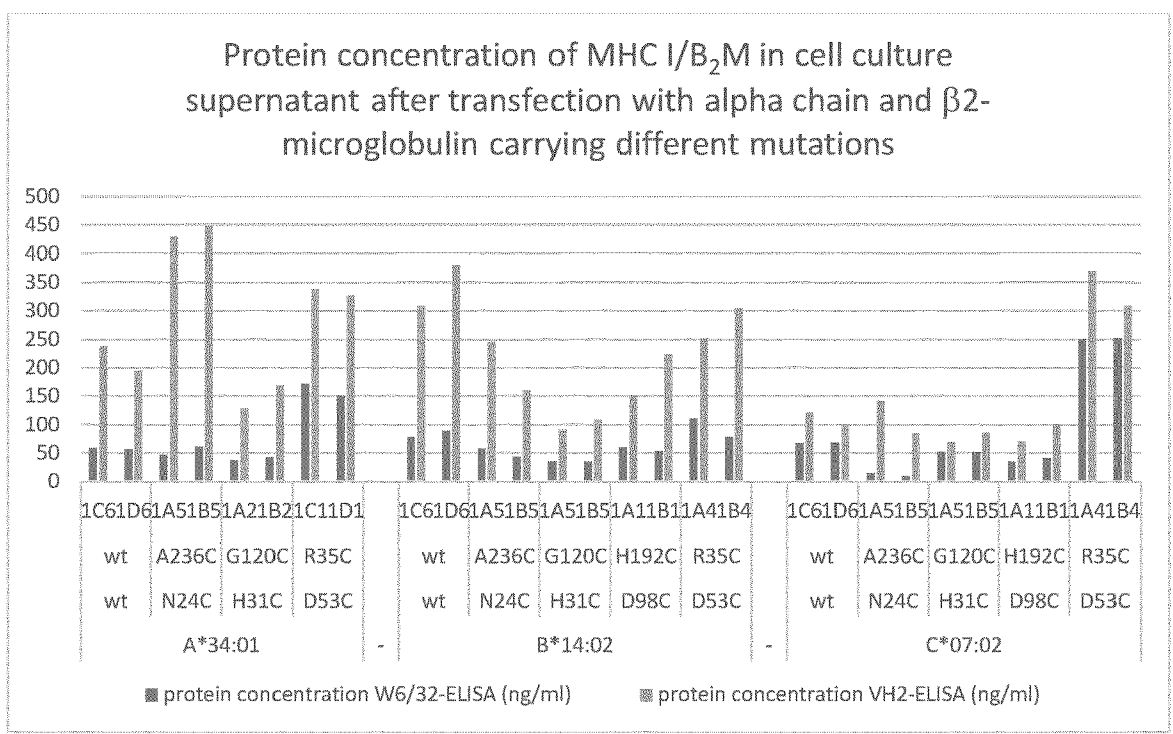
Figure 10:
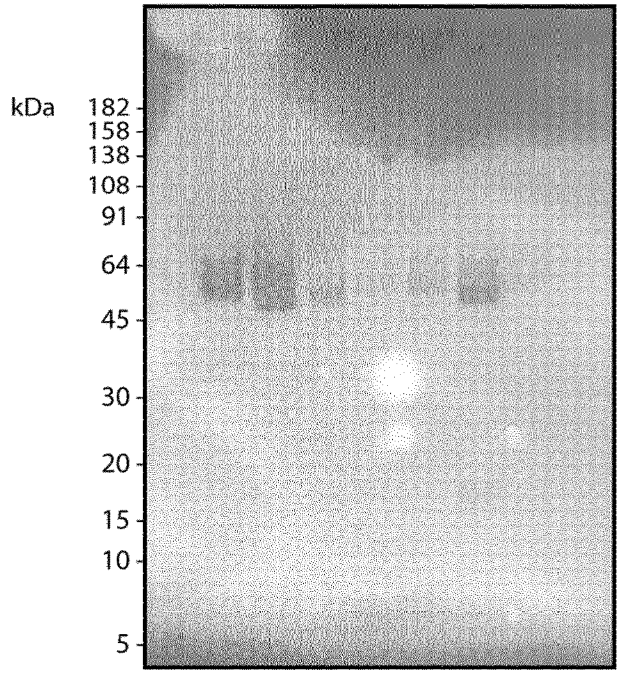

The invention is described in greater detail by way of examples with reference to the figures, which show in FIG. 1 a schematic representation of a preferred expression cassette for the MHC I, FIG. 2 results of detection of embodiments of MHC I molecules, detected with W6/32 antibody, FIG. 3 concentrations of cell culture supernatant of cells expressing embodiments of MHC I molecules and of comparative MHC I molecules, FIG. 4 an SDS-PAGE of purified MHC I according to the invention, FIG. 5 results of an antibody detection assay, and FIG. 6 shows a sequence alignment of exemplary alpha chains of HLA I molecules, indicating AA positions that can be changed to Cystein by al, FIG. 7 a schematic representation of expression cassettes for MHC I alpha chain and β2-microglobulin, FIG. 8 concentrations of cell culture supernatant of cells expressing embodiments of MHC I molecules and of comparative MHC I molecules, FIG. 9 concentrations of cell culture supernatant of cells expressing embodiments of MHC I molecules and of comparative MHC I molecules, FIG. 10 Western Blot of purified cell culture supernatant of cells expressing embodiments of MHC I molecules and of comparative MHC I molecules Example 1: Expression of a Stabilized MHC I Containing One Disulfide Bond FIG. 1 shows a preferred arrangement of sequences encoding the MHC I of the invention, which was used in this Example. From N-terminus to C-terminus, the nucleic acid construct contains directly adjacent one another the coding sequence of a first secretion signal peptide (SP) directly linked to the coding sequence of the alpha chain (alpha chain of MHC class I), directly linked to a tag sequence, herein comprising the tags V5 tag (V5), SBP tag (SBP), and His10 ($His_{10}$), the ribosomal skip sequence P2A, a second secretion signal peptide (SP), and β2-microglobulin β2-m).

As examples for stabilized MHC I molecules which contain only one disulfide bond connecting the alpha chain and the β2-microglobulin, the coding sequence of the alpha chain of HLA-B*55:01 was modified by primer mutagenesis to obtain the G120C mutant which also contained the natural secretion signal peptide coding sequence, and the coding sequence for β2-microglobulin was modified to the H31C mutant which also contained the natural N-terminal secretion signal peptide coding sequence. This combination of Cystein residues corresponds to the pair No. 1 of Cystein residues. Accordingly, the coding sequence did not encode the transmembrane domain of the alpha chain.

These coding sequences were cloned into an expression vector, containing under the control of a SFFV promoter from 5'-terminus to 3'-terminus the coding sequence for the first signal peptide—alpha chain—V5 tag, SBP Tag, His10 tag sequence—the ribosomal skip sequence P2A—second signal peptide—β2-microglobulin.

Similarly, the A236C mutant of the alpha chain of HLA-B*55:01 was expressed in the vector with the R12C mutant of β2-microglobulin, corresponding to pair No. 6 of Cystein residues, and the I23C mutant of the alpha chain of HLA-B*55:01 was expressed in the vector with the L54C mutant of β2-microglobulin, corresponding to pair No. 9 of Cystein residues, and the A236C mutant of the alpha chain of HLA-B*55:01 was expressed in the vector with the N24C mutant of β2-microglobulin, corresponding to pair No. 5 of Cystein residues.

In addition to these mutations of Cystein residues replacing the original amino acids, the β2-microglobulin contained the S55V mutation as described by Shields et al. (1998).

For expression, HEK293 cells were transfected with a viral particle containing the expression cassette in a viral vector. The cells were cultivated under cell culture conditions in DMEM-F12 medium at 37° C. in a 5% $CO_2$ atmosphere. On day 3, culture supernatant was removed, concentrated by isopropanol precipitation and analysed by polyacrylamide gel electrophoresis (SDS-PAGE) for aliquots under non-reducing conditions without dithiothreitol (DTT) or under reducing conditions with DTT added to the sample loading buffer, with subsequent Western blotting onto a PVDF membrane. For detection, the antibody PR1F11F11 that is specific for the V5 tag on the alpha chain, or the BBM.1 antibody that is specific for the β2-microglobulin, each conjugated to horse-radish peroxidase (HRP) for detection, was used.

Using detection of the alpha chain in the Western blot, the comparative wild-type MHC I molecule and the mutant MHC I molecules, all without transmembrane domain, expression and secretion of the MHC I molecules was found in soluble form into the culture supernatant. The results indicate that in the mutant MHC I molecules the disulfide bond is formed between the alpha chain and the β2-microglobulin, resulting in a stabilized association of the alpha chain and the β2-microglobulin.

The β2-microglobulin under non-reducing sample preparation conditions could be shown to be associated with the alpha chain, and under reducing sample preparation conditions could be detected at an apparent size corresponding to the separate β2-microglobulin.

FIG. 2 shows the results of an ELISA, normalized to wildtype soluble MHC I, in which culture supernatant of cells expressing MHC I molecules was immobilized on a BBM.1 antibody coated surface and detection was by W6/32 antibody, which is generally regarded as indicating a non-denatured or natural conformation of MHC I molecules. For comparison, supernatant of a HEK293 cell expressing the wild-type alpha chain without transmembrane domain and the S55V variant of β2-microglobulin (WT/S55V) and supernatant of wild-type alpha chain without transmembrane domain and the wild-type of β2-microglobulin (WT/WT) were included. The stabilized MHC I molecules were A236C in the alpha chain and N24C in the β2-microglobulin (pair No. 5, A236C/N24C_S55V), also carrying the S55V mutation, and G120C in the alpha chain and H31C in the β2-microglobulin (pair No. 1, G120C/H31C_S55V), also carrying the S55V mutation in the β2-microglobulin. The results show that the MHC I molecules stabilized by a disulfide bridge have a natural conformation, as determined by binding of the W6/32 antibody.

Further, HEK293 cells were transfected with a nucleic acid construct encoding the stabilized mutant of HLA-B*55:01, carrying the G120C mutation in the alpha chain and the H31C mutation in the β2-microglobulin in the same vector as described above (pair No. 1, G120C/H31C), or the cells were transfected with a nucleic acid construct encoding the stabilized mutant of HLA-B*55:01, carrying the G120C mutation in the alpha chain and the I1C mutation in the β2-microglobulin in the same vector as described above (pair No. 2, G120C/I1C) as a repetition, cell culture supernatants were shown to contain the stabilized mutant MHC I molecules that have the disulfide bond between the alpha chain and the β2-microglobulin.

Using a Western blot of cell culture supernatants with sample preparation under non-reducing conditions, i.e. using SDS containing sample buffer without DTT (−DTT) and detection with HRP-conjugated antibody directed against the β2-microglobulin (BBM.1-HRP), it could be shown that the stabilized MHC I molecules and also the natural B*55:01 molecule used as a comparison, which was expressed in the same cell type from the nucleic acid construct containing the same signal peptides and regulatory elements, contain the β2-microglobulin in association with the alpha chain (band of apparent 58 kDa). In contrast, the wild-type comparative natural B*55:01 molecule shows a more prominent band of β2-microglobulin that is dissociated from the alpha chain. An additional detected band of apparent 14-15 kDa in the lanes of the stabilized MHC I molecules was assumed to be β2-microglobulin that has not formed a disulfide bond with an alpha chain.

Using a Western blot of an SDS-PAGE using reducing sample preparation conditions (+DTT) of the same cell culture supernatants with detection by a HRP-conjugated antibody (PR1F11F11-HRP) directed against the V5 tag on the alpha chain, it could be shown that the stabilized MHC I molecules under reducing conditions show a lower apparent molecular weight than under non-reducing conditions, which weight corresponds to the size of the alpha chain only, indicating dissociation of the β2-microglobulin chain under reducing conditions.

Analysis of an ELISA as above using immobilized cell culture supernatants and detection by anti-tag antibody (anti-V5His) or detection by W6/32 antibody could show that in this assay the stabilized MHC I molecule containing the disulfide bond formed by pair No. 1, G120C/H31C (B5501_G120C_b2m_H31C) is strongly recognized by the W6/32 antibody, indicating a conformation corresponding to that of natural MHC I. A signal for the anti-tag antibody was detected at lower intensity, indicating that the tag is present in the stabilized MHC I molecule but is assumed to be less accessible than the binding site for W6/32 antibody.

FIG. 3 shows concentrations of MHC I molecules in stably transduced cell culture supernatant in a 25 $cm^2$ cell culture flask, detected using a sandwich ELISA with the BBM.1 and the W6/32 antibody. This shows that along with the positive control of wildtype MHC I containing both alpha chain and β2-microglobulin in wild-type form (wt/wt), the mutant having the S55V in the β2-microglobulin with a wild-type alpha chain (wt/S55V) and the stabilized MHC I G120C/H31C (G120C/H31C_S55V) including the S55V in the β2-microglobulin, and the stabilized MHC I A236C/N24C (A236C/N24C_S55C), all without transmembrane domain, are expressed in the cell culture from the construct containing the coding sequences under the control of one promoter only with a ribosomal skip sequence arranged between these.

From separate cultures, the cell culture supernatant was collected and buffered into PBS (7 mM NaH2PO4, 150 mM NaCl, pH 7.4). HLA-B*55:01 protein was bound to an immobilized metal affinity chromatography (IMAC) column via the histidine tag, the column was washed, and bound protein was eluted with imidazol, to yield (wt/wt), (wt/S55V), and (G120C/H31C_S55V) in separate preparations. The eluates were buffered into PBS, optionally containing a preserving agent, e.g. ProClin 300 (obtainable from Sigma Aldrich), adjusted to 400 to 500 ng/mL, and stored at 4° C.

FIG. 4 shows a Coomassie stained SDS-PAGE of the preparation, under reducing and non-reducing conditions. In the lanes of the MHC I (HLA-B*55:01) wild-type (WT) alpha chain associated with the wild-type (WT) β2-microglobulin ($B_2M$) or with the S55V mutant β2-microglobulin, the sample without DTT (−) migrate to apparent lower molecular weights, which is assumed to be due to increased compactness of the alpha chain and β2-microglobulin in their associated state, than the sample with DTT (+). For the MHC I of the alpha chain having the G120C mutation (G120C) and the β2-microglobulin having the H31C and the S55V mutations (H31C/S55V), the lane without DTT (−) shows a prominent band of higher molecular weight than the prominent band of the wild-types, and the lane with DTT (−) shows a lower molecular weight than the one with DTT. Only in the presence of DTT, the MHC I of the alpha chain having the G120C mutation (G120C) and the β2-microglobulin having the H31C and the S55V mutations shows a band of 11 kDa, corresponding to an isolated β2-microglobulin chain, and the lane without DTT shows no band corresponding to the isolated β2-microglobulin chain. The results confirm the disulfide bond between alpha chain and isolated β2-microglobulin chain for the exemplary MHC I of the invention.

Example 2: Analysis of Antibody from a Serum Sample

Samples: Positive serum known to contain an anti-HLA B*55:01 antibody; Negative serum without anti-HLA antibodies; Positive control: anti-$B_2M$ antibody (BBM.1), HRP-coupled.

Protocol:

Wash the required amount of Dynabeads M-280 streptavidin (M280SA; Thermo Fisher, 2.5 μl per well of a 96-well-plate) with TSP (50 mM tris(hydroxymethyl)amino methane-hydrochloride, 0.5 mM ethylenediamine tetraacetic acid (EDTA), 100 mM sodium chloride, 0.1% v/v ProClin300, 5% w/v saccharose, adjust to pH 8.0)/10% PBSTB (7 mM NaH2PO4, 150 mM NaCl, pH 7.4, 0, 05% v/v Tween 20, 2% w/v bovine serum albumin), resuspend in starting volume. Distribute 2.5 μl M280SA into the required wells of a 96 well plate (Nunc, 96F). Add 0.5 μg of HLA-B*55:01 (G120C/H31C_S55V) to 2.5 μl M280SA beads in 100 μl TSP/10% PBSTB. Resuspend the beads, incubate overnight at 2 to 8° C., wash 5× with a magnetic washer (HydroFlex microplate washer, Tecan) with PIWP (1.9 mM di-sodium hydrogenphosphate ($Na_2HPO_4$), 0.07 mM sodium dihydrogenphosphate ($NaH_2PO_4$), 0.05% w/v Tween 20, 1 μM 2-bromo-2-nitro-1,3-propandiol). Add 100 μl serum 1:8 dilution in BAP (PBS, 1% w/v bovine serum albumin, 0.05% Tween20, 0.1% w/v ProClin300), only BAP, or anti-β2-microglobulin antibody at dilution of 1:2,500 in BAP, respectively. Resuspend the beads and incubate for 45 min at room temperature. Wash 5 times with a magnetic washer with PIWP. Add to all wells 100 μl anti human IgG antibody (MCA647P, Bio-Rad, HRP coupled) at dilution of 1:20,000 in PIKV (50% v/v fetal calf serum, 1.06% v/v tris(hydroxymethyl)amino methane, 0.5% w/v PVP-10 (polyvinyl pyrrolidone, average mol. weight 10 000), 0.45% w/v NaCl, 0.1% w/v Ca-propionate, optionally 0.2% v/v ProClin 300, 0.05% w/v 8-anilino-1-naphthalene sulfonic acid (ANS), 0.025% penicillin, 0.025% streptomycin, adjusted to pH 7.35). Incubate for 45 min at room temperature in the dark. Wash 5 times with a magnetic washer with PIWP. Add 100 μl TMB ONE (obtained from Kem-En-Tec Diagnostics, Denmark). Incubate for 15 min at room temperature in the dark while shaking. Stop reaction by adding 100 μl stop solution (5% v/v $H_2SO_4$). Absorbance was measured in a microtiter plate reader (Powerwave 320, Bio-Tek) at 450 nm and at 690 nm (background scatter from the beads), from which the difference was calculated ($OD_{450\text{-}690\ nm}$). FIG. 5 shows the result of the experiment. The positive serum shows a clearly distinguishable signal from the negative serum and the no-antibody-well. The positive control confirms the presence of antigen in the well.

Example 3: Expression of a Stabilized MHC I Containing One Disulfide Bond

FIG. 7 shows the arrangement of expression vectors used in this example, vector 1 coding for the alpha chain of MHC I and vector 2 coding for β2-microglobulin. From N-terminus to C-terminus, the nucleic acid construct vector 1 contains directly adjacent one another the coding sequence of a secretion signal peptide (SP) directly linked to the coding sequence of the alpha chain (alpha chain of MHC class I), directly linked to a tag sequence (VX), herein comprising the tags V5 tag (V5), and His10 ($His_{10}$). Vector 2 contains a signal peptide (SP), directly linked to the β2-microglobulin β2-m) coding sequence.

In this example the MHC I alleles HLA-A*02:01, HLA-A*34:01, HLA-A*68:01, HLA-B*14:02 and HLA-C*07:02 were chosen for comparison of expression levels of different Cystein mutants. For each Cystein mutant one expression vector was created by primer mutagenesis. Cystein residues on alpha chain are A236C, D119C, G120C, and I23C. Cystein residues on β2-microglobulin are I1C, N24C, H31C, and L54C.

The A236C mutant of the alpha chain was expressed together with the N24C mutant of β2-microglobulin, corresponding to pair No. 5 of Cystein residues, and the D119C mutant of the alpha chain was expressed together with the I1C mutant of β2-microglobulin as a comparative example, and the G120C mutant of the alpha chain was expressed together with the H31C mutant of β2-microglobulin, corresponding to pair No. 1 of Cystein residues, and the G120C mutant of the alpha chain was expressed together with the I1C mutant of β2-microglobulin, corresponding to pair No. 2 of Cystein residues, and the I23C mutant of the alpha chain was expressed together with the L54C mutant of β2-microglobulin, corresponding to pair No. 9 of Cystein residues.

The expression vectors did not contain a coding sequence for a transmembrane domain, and no coding sequence for a cognate antigenic peptide.

For expression HEK293 cells were transfected with an expression vector coding for the alpha chain of MHC I and an additional expression vector coding for β2-microglobulin using a transfection reagent (Xfect™, Takara Bio Inc.). The cells were seeded in 24-well-plates, each well containing 1 ml of cell culture medium. The cells were cultivated under cell culture conditions in DMEM-F12 medium with 2% FCS at 37° C. in a 5% $CO_2$ atmosphere. On day 3, culture supernatant was removed and protein expression was analysed by an ELISA.

FIG. 8 shows the results of the ELISA, in which culture supernatant of cells expressing MHC I molecules was immobilized on a BBM.1 or PR1F11F11 (anti-V5 tag) antibody coated surface and detection was by W6/32 or anti-His antibody. The anti-His tag antibody indicates MHC I protein concentration (right hand columns), the W6/32 antibody indicates native MHC I conformation (left hand columns). For comparison, supernatant of a HEK293 cell expressing the wild-type alpha chain without transmembrane domain the wild-type of β2-microglobulin (WT/WT) were included.

The result depicted in FIG. 8 shows that the comparative MHC I mutant, containing a Cystein in amino acid No. 119 of the alpha chain and a Cystein in amino acid No. 1 of the β2-microglobulin for HLA-A*02:01, for HLA-A*34:01, and for HLA-A*68:01 did not express an MHC I molecule. For the MHC I molecules of the invention, both expression and confirmation of the natural MHC I conformation by the conformation-specific antibody W6/32 was found.

Further comparative exemplary combinations contained the Q96C mutation in the alpha chain and the W60C mutation in the β2-microglobulin, and the Q96C mutation in the alpha chain and the H31C mutation in the β2-microglobulin. These comparative MHC I molecules were not expressed in a natural conformation as determined by the W6/32 antibody ELISA.

Example 4: Expression of a Stabilized MHC I Containing One Disulfide Bond

For this example the MHC I alleles HLA-A*34:01, HLA-B*14:02, and HLA-C*07:02 were selected for comparison of expression levels of different Cystein mutants. Cystein residues on alpha chain are A236C, G120C, H192C, and R35C. Cystein residues on β2-microglobulin are N24C, H31C, D98C, and L54C.

The A236C mutant of the alpha chain was expressed together with the N24C mutant of β2-microglobulin, corresponding to pair No. 5 of Cystein residues, and the G120C mutant of the alpha chain was expressed together with the H31C mutant of β2-microglobulin, corresponding to pair No. 1 of Cystein residues, and the R35C mutant of the alpha chain was expressed together with the D53C mutant of β2-microglobulin, corresponding to pair No. 3 of Cystein residues. The 192C mutant of the alpha chain was expressed together with the 98C mutant of β2-microglobulin, corresponding to pair No. 12 of Cystein residues.

For expression, HEK293 cells were transfected with an expression vector coding for the alpha chain of MHC I and an additional expression vector coding for β2-microglobulin using a transfection reagent (Xfect™, Takara Bio Inc.). HLA-A*34:01, HLA-B*14:02, and HLA-C*07:02 were selected as alleles for the alpha chain. The cells were seeded in 24-well-plates, each well containing 1 ml of cell culture medium. The cells were cultivated under cell culture conditions in DMEM-F12 medium with 2% FCS at 37° C. in a 5% $CO_2$ atmosphere. On day 3, culture supernatant was removed and protein expression was analysed by ELISA.

FIG. 9 shows the results of the ELISA, in which culture supernatant of cells expressing MHC I molecules was immobilized on a BBM.1 or PR1F11F11 (anti-V5 tag) antibody coated surface and detection was by W6/32 indicating native MHC I conformation (left hand columns) or anti-His antibody indicating MHC I protein concentration (right hand columns). For comparison, supernatant of a HEK293 cell expressing the wild-type alpha chain without transmembrane domain the wild-type of β2-microglobulin (WT/WT) were included.

The result shows that these MHC I molecules were expressed in natural MHC I conformation as determined by W6/32 ELISA.

Certain samples of cell supernatant were further buffered into PBS (7 mM $NaH_2PO_4$, 150 mM NaCl, pH 7.4) and purified by IMAC. Purified samples were run under non-reducing conditions on an SDS-PAGE with subsequent Western blotting onto a PVDF membrane. For detection the BBM.1 antibody that is specific for the β2-microglobulin, conjugated to horse-radish peroxidase (HRP) for detection, was used.

The result is shown in FIG. 10, indicating that these exemplary MHC I molecules of the invention were expressed, running at similar apparent sizes in the non-reducing SDS-PAGE, the size indicating that a single disulfide bond was formed between the alpha chain and β2-microglobulin.

The examples show that the MHC I molecules of the invention, which lack a covalently bound cognate antigenic peptide and have no transmembrane domain, can be expressed in cell culture and have a native MHC I conformation.

The invention claimed is:

1. An MHC I molecule comprising an alpha chain and a β2-microglobulin being devoid of a covalently linked cognate antigenic peptide while comprising at least one covalent bond that is formed between Cysteine residues of the pairs of amino acid residues selected from

| Pair No. | Amino acid position of alpha chain | Amino acid position of β2-microglobulin |
|---|---|---|
| 1 | No. 120 | No. 31, |

wherein the alpha chain has at least 90% sequence identity with amino acids No. 3 to 272 of SEQ ID NO: 1, SEQ ID NO: 2, SEQ ID NO: 3, or SEQ ID NO: 9, and the β2-microglobulin has at least 90% sequence identity with SEQ ID NO: 4, wherein the numbering of amino acid positions in the alpha chain and in the β2-microglobulin refers to the alpha chain (SEQ ID NOS: 1-3 or SEQ ID NO: 9) and the β2-microglobulin (SEQ ID NO: 4) without an N-terminal signal peptide.

2. The MHC I molecule according to claim 1, having no transmembrane domain.

3. The MHC I molecule according to claim 1, comprising a transmembrane domain linked to the C-terminus of the alpha chain.

4. The MHC I molecule according to claim 3, bound to a cell membrane via its transmembrane domain.

5. The MHC I molecule according to claim 1, wherein the alpha chain comprises or consists of the amino acids No. 3 to No. 272 of SEQ ID NO: 1, SEQ ID NO: 2, SEQ ID NO: 3, or SEQ ID NO: 9, wherein the numbering refers to the peptide chain without an N-terminal signal peptide.

6. The MHC I molecule according to claim 1, wherein the β2-microglobulin comprises or consists of the amino acids No. 3 to No. 97 of SEQ ID NO: 4, wherein the numbering refers to the peptide chain without an N-terminal signal peptide.

7. The MHC I molecule according to claim 1, wherein the β2-microglobulin comprises a Valin at amino acid position 55, a mutation K58E, or S55V, wherein the alpha chain comprises one or more mutations selected from the group consisting of 74L, 223A, 224E, 225D, 226A, 227K, 229A, 245V, 227K, 228A, 139C, 84C, 85C, and 115E, wherein the numbering of amino acid positions in the alpha chain and β2-microglobulin refers to the peptide chain without an N-terminal signal peptide.

8. A process for producing a modified MHC I molecule according to claim 1 by expressing at least one nucleic acid sequence encoding the modified MHC I molecule in a mammalian cell culture, in an insect cell culture, or in a yeast or fungal culture, or in a prokaryotic cell culture.

9. The process according to claim 8, wherein the MHC I molecule under the control of one promoter is encoded by a nucleic acid sequence comprising from 5' to 3' the following elements: optional first signal peptide-alpha chain—optional tag sequence—ribosomal skip sequence—optional second signal peptide—β2-microglobulin.

10. The process according to claim 8, wherein the alpha chain and the β2-microglobulin are encoded by separate expression cassettes which are contained together in the cells of the mammalian cell culture, of the insect cell culture, or the yeast or fungal culture, or in a prokaryotic cell culture.

11. An analytical process for determining the reaction of a biological sample with an MHC I molecule, comprising contacting the biological sample with the MHC I molecule according to claim 1, and determining whether a portion of the biological sample binds to the MHC I molecule.

12. The analytical process according to claim 11, wherein the biological sample comprises a sample of a patient and wherein the analytical method further comprises providing a result of the analytical process to the patient or to a medic appointed by the patient.

13. The MHC I molecule according to claim 1, wherein the alpha chain has at least 95% sequence identity with amino acids No. 3 to 272 of SEQ ID NO: 1, SEQ ID NO: 2, SEQ ID NO: 3, or SEQ ID NO: 9, and the β2-microglobulin has at least 95% sequence identity with SEQ ID NO: 4.

* * * * *